US008513007B2

(12) United States Patent
Penn et al.

(10) Patent No.: US 8,513,007 B2
(45) Date of Patent: *Aug. 20, 2013

(54) SDF-1 DELIVERY FOR TREATING ISCHEMIC TISSUE

(75) Inventors: Marc S. Penn, Beachwood, OH (US); Rahul Aras, Broadview Heights, OH (US); Joseph Pastore, Mentor, OH (US); Timothy J. Miller, Cleveland Heights, OH (US)

(73) Assignees: The Cleveland Clinic Foundation, Cleveland, OH (US); Juventas Therapeutics, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/556,639

(22) Filed: Jul. 24, 2012

(65) Prior Publication Data
US 2012/0289586 A1 Nov. 15, 2012

Related U.S. Application Data

(63) Continuation of application No. 13/393,141, filed as application No. PCT/US2010/047175 on Aug. 30, 2010.

(60) Provisional application No. 61/237,775, filed on Aug. 28, 2009, provisional application No. 61/334,216, filed on May 13, 2010.

(51) Int. Cl.
*A61K 48/00* (2006.01)
*C12N 15/00* (2006.01)

(52) U.S. Cl.
USPC .................... 435/320.1; 514/44 R

(58) Field of Classification Search
None
See application file for complete search history.

(56) References Cited

U.S. PATENT DOCUMENTS

| 3,773,919 | A | 11/1973 | Boswell |
| 5,197,985 | A | 3/1993 | Caplan et al. |
| 5,980,887 | A | 11/1999 | Isner et al. |
| 6,100,242 | A | 8/2000 | Hammond |
| 6,121,246 | A | 9/2000 | Isner |
| 6,121,428 | A | 9/2000 | Blank et al. |
| 6,358,697 | B2 | 3/2002 | Rothenberg |

(Continued)

FOREIGN PATENT DOCUMENTS

| EP | 1803464 A1 | 7/2007 |
| JP | 2004099471 | 2/2004 |

(Continued)

OTHER PUBLICATIONS

Konstan et al. (2004) Compacted DNA nanoparticles administered to the nasal mucosa of cystic fibrosis subjects are safe and demonstrate partial to complete cystic fibrosis transmembrane regulator reconstitution. Human Gene Therapy 15: 1-15.*

(Continued)

*Primary Examiner* — Anne-Marie Falk
(74) *Attorney, Agent, or Firm* — Woodcock Washburn LLP

(57) ABSTRACT

A method of treating a cardiomyopathy in a subject includes administering directly to or expressing locally in a weakened, ischemic, and/or peri-infarct region of myocardial tissue of the subject an amount of SDF-1 effective to cause functional improvement in at least one of the following parameters: left ventricular volume, left ventricular area, left ventricular dimension, cardiac function, 6-minute walk test, or New York Heart Association (NYHA) functional classification.

6 Claims, 8 Drawing Sheets

(56) References Cited

U.S. PATENT DOCUMENTS

| | | |
|---|---|---|
| 6,479,654 B1 | 11/2002 | Baird |
| 6,818,210 B2 | 11/2004 | Field |
| 7,101,708 B1 | 9/2006 | Lapidot et al. |
| 7,125,856 B1 | 10/2006 | Isner |
| 7,141,363 B2 | 11/2006 | Poznansky et al. |
| 7,393,628 B2 | 7/2008 | Wagner et al. |
| 7,393,830 B2 | 7/2008 | Shingo et al. |
| 7,396,537 B1 | 7/2008 | Krupnick |
| 7,396,680 B2 | 7/2008 | Shmelkov et al. |
| 7,399,740 B2 | 7/2008 | Eisenbach-Schwartz et al. |
| 7,399,751 B2 | 7/2008 | Kirkpatrick |
| 7,402,567 B2 | 7/2008 | Chojkier et al. |
| 7,402,724 B2 | 7/2008 | Conover |
| 7,405,076 B2 | 7/2008 | Goldman |
| 7,405,195 B2 | 7/2008 | Chen et al. |
| 7,662,392 B2 | 2/2010 | Itescu |
| 2002/0039993 A1 | 4/2002 | Winchester et al. |
| 2002/0061587 A1 | 5/2002 | Anversa |
| 2002/0094327 A1 | 7/2002 | Peterson |
| 2002/0107195 A1 | 8/2002 | Gupta |
| 2002/0111290 A1 | 8/2002 | Homey et al. |
| 2003/0199464 A1 | 10/2003 | Itescu |
| 2004/0037811 A1 | 2/2004 | Penn |
| 2004/0235160 A1 | 11/2004 | Nishikawa et al. |
| 2004/0258669 A1 | 12/2004 | Dzau et al. |
| 2004/0258670 A1 | 12/2004 | Laughlin et al. |
| 2005/0271639 A1 | 12/2005 | Penn |
| 2006/0105950 A1 | 5/2006 | Losordo |
| 2006/0166361 A1 | 7/2006 | Seyda |
| 2007/0056595 A1 | 3/2007 | McLachlan |
| 2007/0173471 A1 | 7/2007 | Losordo |
| 2007/0224171 A1 | 9/2007 | Penn |
| 2007/0258943 A1 | 11/2007 | Penn |
| 2010/0166717 A1 | 7/2010 | Penn |
| 2010/0272679 A1 | 10/2010 | Penn |

FOREIGN PATENT DOCUMENTS

| | | |
|---|---|---|
| WO | WO 92/08796 | 5/1992 |
| WO | WO 94/28143 | 12/1994 |
| WO | WO 99/20759 A1 | 4/1999 |
| WO | WO 99/45775 | 9/1999 |
| WO | WO 99/50461 A1 | 10/1999 |
| WO | WO 00/19442 A1 | 4/2000 |
| WO | WO 00/50048 A2 | 8/2000 |
| WO | WO 00/60086 A2 | 10/2000 |
| WO | WO 01/94420 A1 | 12/2001 |
| WO | WO 03/014336 | 2/2003 |
| WO | WO 03/059375 | 7/2003 |
| WO | WO 03/105908 | 12/2003 |
| WO | WO 2004/093688 | 11/2004 |
| WO | WO 2005/047494 A2 | 5/2005 |
| WO | WO 2006/030887 | 3/2006 |
| WO | WO 2008/121719 | 10/2008 |
| WO | WO 2011/026041 A2 | 3/2011 |
| WO | WO 2012/037083 A2 | 3/2012 |

OTHER PUBLICATIONS

U.S. Appl. No. 13/556,595, filed Jul. 24, 2012, Penn.

Abbott et al., "Stromel cell-derived factor-1alpha plays a critical role in stem cell recruitment to the heart after myocardial infarction but is not sufficient to induce homing in the absence of injury", Circulation, Nov. 23, 2004, 110(21), 3300-3305.

Asahara et al, "VEGF contributes to postnatal neovascularization by mobilizing bone marrow-derived endothelial progenitor cells.", EMBO J., Jul. 15, 1999, 18(14), 3964-3972.

Askari et al., "Effect of stromal-cell-derived factor 1 on stem-cell homing and tissue regeneration in ischemic cardiomyopathy", The Lancet, Aug. 30, 2003, 362(9385), 697-703.

Badillo et al, "Lentiviral gene transfer of SDF-1α to wounds improves diabetic wound healing", Journal of Surgical Research, Nov. 2007, 143(1), 35-42.

Bauman et al, CXCR-4 transduced human mesenchymal stem cells (MSCs) migrate in response to SDF-1alpha., blood, 2001, 98(11 Part1), P87a.

Baumgartner et al, "constitutive expression of phVEGF165 after intramuscular gene transfer promotes collateral vessel development in patients with critical limb ischemia.", Circulation, Mar. 31, 1998, 97(12), 1114-1123.

Cheng et al, Targeted migration of mesenchymal stem cells modified with CXCR4 gene to infarcted myocardium improves cardiac performance. Molecular Therapy, Mar. 16, 2008, 16(3), 571-579, E-publication Feb. 5, 2008.

Daley et al, "Prospects for stem cell-based therapy", Cell, Feb. 22, 2008, 132(4), 544-548.

Deten et al, "Hematopoietic stem cells do not repair the infarcted mouse heart" Cardiovascular Research, Jan. 1, 2005, 6591), 52-63.

Elmadbouh et al., "Ex vivo delivered stromal cell-derived factor-1alpha promotes stem cell homing and induces angiomyogenesis in the infarcted myocardium", Journal of Molecular and Cellular Cardiology, Apr. 2007, 42(4), 792-803.

Etzion et al, "Influence of embryonic cardiomyocyte transplantation on the progression of heart failure in a rat model of extensive myocardial infarction.", J. Mol. Cell Cardiol., Jul. 2001, 33(7), 1321-1330.

Ewaga et al, "the earliest stages of B cell development require a chemokine stromal cell-derived factor/preB cell growth-stimulating factor", Immunity, Aug. 15, 2001, 15, 323-334.

Freedman et al, "Therapeutic angiogenesis for coronary artery disease.", Annals Internal Medicine, Jan. 1, 2002, 136(1), 54-71.

Gallagher et al, "Diabetic impairments in NO-Mediated endothelial progenitor cell mobilization and homing are reversed by hyperoxia and SDF-1α", The Journal of clinical investigation, May 2007, 117(5), 1249-1259.

Ghadge et al, SDF-1a as a therapeutic Stem cell homing factor in myocardial infarction, Pharmacology & Therapeutics, Jan. 2011, 129(1), 97-108.

Grines et al, "Angiogenic gene therapy (AGENT) trial in patients with stable angina pectoris.", Circulation, Mar. 19, 2002, 105(11), 1291-1297.

Haider et al, "IGF-1—Overexpressing Mesenchymal Stem Cells Accelerate Bone Marrow Stem Cell Mobilization via Paracrine Activation of SDF-1α/CXCR4 Signaling to Promote Myocardial Repair", Circulation Research, Nov. 21, 2008, 103(11), 1300-1398.

Hariawala et al, "VEGF improves myocardial blood flow but produces EDRF-mediated hypotension in porcine hearts.", J. Surg. Res. Jun. 1996, 63(1), 77-82.

Hattori et al, Plasma elevation of stromal cell-derived factor-1 induces mobilization of mature and immature hematopoietic progenitor and stem cells, Blood, Jun. 1, 2001, 97(11), 3354-3360.

Hiasa et al, "Gene transfer of stromal cell-derived factor-1α enhances ischemic vasculogenesis and angiogenesis via vascular endothelial growth factor/endothelial nitric oxide synthase-related pathway", Circulation, May 25, 2004, 1009, 2454-2461.

Holden et al, "Plasticity: Time for a reappraisal?", Science, Jun. 21, 2002, 296(5576), 2126-2129.

Hu et al, "Stromel cell-derived factor-1α confers protection against myocardial ischemia/reperfusion injury", Circulation, Aug. 7, 2007, 116(6), 654-663.

Jackson et al, "Regeneration of ischemic cardiac muscle and vascular endothelium by adult stem cells.", J. Clin. Invest., Jun. 2001, 107(11), 1395-1402.

Jain et al, "cell therapy attenuates deleterious ventricular remodeling and improves cardiac performance after myocardial infarction.", Circulation, Apr. 10, 2001, 103, 1920-1927.

Jaleel et al., "Stromel cell-derived factor-1 (SDF-1) signaling regulates human placental trophoblast cell survival", Molecular Human Reproduction, Oct. 8, 2004, 10(12), 901-909.

Jo et al, "Chemotaxis of primitive hematopoietic cells in response to stromal cell-derived factor-1", J.Clin. Invest., Jan. 2000, 105(1), 101-111.

Kahn et al, Overexpression of CXCR4 on human CD34+ progenitors increases their proliferation, migration, and NOD/SCID repopulation, Blood, Apr. 15, 2004, 103(8), 2942-2949.

Kim, Chang H., and Broxmeyer, Hal E., In Vitro behavior of hematopoietic progenitor cells under the influence of chemoattractants: stromal cell-derived factor-1, steel factor, and the bone marrow environment, Blood, Jan. 1, 1998, 91(1), 100-110.

Kitaori et al, Stromal Cell-derived factor 1/CXCR4 signaling is critical for the recruitment of mesenchymal stem cells to the fracture site during skeletal repair in a mouse model Arthritis & Rheumatism, Mar. 2009, 60(3), 813-823.

Koch et al, "Effect of catheter-based transendocardial delivery of stromal cell-derived factor 1α on left ventricular function and perfusion in a porcine model of myocardial infarction", Basic Research in Cardiology, Jan. 2006, 101(1), 69-77.

Kocher et al, "Neovascularization of ischemic myocardium by human bone-marrow-derived angioblasts prevents cardiomyocyte apoptosis, reduces remodeling and improves cardiac function.", Nat. Med. Apr. 2001, 7(4), 430-436.

Koh et al, "Differentiation and long-term survival of C2C12 Myoblast grafts in heart.", J. Clin. Invest., Sep. 1993, 92(3), 1548-1554.

Koh et al, Targeted Expression of transforming growth factor-beta 1 in intracardiac grafts promotes vascular endothelial cell DNA synthesis., J. Clin. Invest., Jan. 1995, 95(1), 114-121.

Kusano et al, "Sonic hedgehog myocardial gene therapy: Tissue repair through transient reconstitution of embryonic signaling", Nature Medicine, Nov. 2005, 11(11), 1197-1204.

Laham et al, "Local perivascular delivery of basic fibroblast growth factor in patients undergoing coronary bypass surgery: Results of a phase I randomized, Double-blind, placebo-controlled trail." Circulation, Nov. 2, 1999, 100(18), 1865-1871.

Lapidot et al, Current understanding of stem cell mobilization: The roles of chemokines, proteolytic enzymes, adhesion molecules, and stromal cells, Experimental Hematology, Sep. 2002, 30(9), 973-981.

Lataillade et al., "Stromel cell-derived factor 1 regulates primitive hematopoiesis by suppressing apoptosis and by promoting G(0)/G(1) transition in CD34(+) cells: evidence for an autocrine/paracrine mechanism", Blood, Feb. 15, 2002, 99(4), 1117-1129.

Lee et al, "VEDG gene delivery to myocardium: deleterious effects of unregulated expression.", Circulation, Aug. 2000, 102(8), 898-901.

Lee et al, Functional Analysis of the Endothelin-1 Gene Promoter, The Journal of Biological Chemistry, Jun. 1990, 265(18), 10446-10450.

Li et al, "Cardiomyocyte transplantation improves heart function", Ann Thorac. Surg. Sep. 1996, 62(3), 654-660.

Lopez et al, "Hemodynamic effects of intracoronary VEGF delivery: Evidence of tachyphylaxis and No dependence of response.", Am. J. Physiol., Sep. 1997, 273, (3 Pt2), H1317-H1323.

Ma et al, "Impaired B-Lymphopoiesis, Myelopoiesis, and derailed cerebellar neuron migration in CXCR4-and SDF-1-deficient mice", Proc. Natl. Acad. Sci, USA, Aug. 1998, 95(16), 9448-9453.

Matteucci, M.D., and Caruthers, M.H., "Synthesis of Deoxyoligonucleotides on a Polymer Support", J. Am. Chem. Soc., 1981, 103, 3185-3191.

Menasche et al, "Myoblast transplantation for heart failure.", Lancet, Jan. 27, 2001, 357(9252), 279-280.

Murry et al, Haematopoietic stem cells do not transdifferentiate into cardiac myocytes in myocardial infarcts, Nature, Apr. 8, 2004, 428(6983), 664-668, Epublication Mar. 21, 2004.

Nagasawa et al, "Defects of B-cell lymphopoiesis and Bone-marrow myelopoiesis in mice lacking the CXC Chemokine PBSF/SDF-1.", Nature, Aug. 15, 1996, 382(6952), 635-638.

Nakayama et al, "Vascular endothelial growth factor synergistically enhances bone morphogenetic protein-4-dependent lymphohematopoietic cell generation from embryonic stem cells in vitro.", blood, Apr. 1, 2000, 95(7), 2275-2283.

Norol et al, "Influence of mobilized stem cells on myocardial infarct repair in a nonhuman primate model", Dec. 15, 2003, Blood, 102(13), 4361-4368.

Ohtsuka et al, "Cytokine therapy prevents left ventricular remodeling and dysfunction after myocardial infarction through neovascularization", FASEB, May 2004, 18, 851-853.

Onai et al, Impairment of lymphopoiesis and myelopoiesis in mice reconstituted with bone marrow-hematopoietic progenitor cells expressing SDF-1-intrakine., Blood, Sep. 15, 2000, 96(6), 2074-2080.

Orlic et al, "Bone marrow cells regenerate infarcted myocardium.", Nature, Apr. 5, 2001, 410(6829), 701-705.

Orlic et al, "Mobilized bone marrow cells repair the infarcted heart, improving function and survival", PNAS, Aug. 28, 2001, 98(18), 10344-10349.

Peled et al, "The chemokine SDF-1 activates the integrins LFA-1, VLA-4, and VLA-5 on Immature human CD34(+) cells: role transendothelial/stromal migration and engraftment of NOD/SCID mice". Blood, Jun. 1, 2000, 95(11), 3289-3296.

Penn et al, Autologous cell transplantation for the treatment of damaged myocardium, Progress in cardiovascular diseases, Jul. 2002, 45(1), 21-32.

Penn et al, Role of stem cell homing in myocardial regeneration, international journal of cardiology, Jun. 2004, 95, S23-S25.

Pfeffer et al, "Ventricular remodeling after myocardial infarction. Experimental observations and clinical implications.", Circulation, Apr. 1990, 81(4), 1161-1172.

Quaini et al, "Chimerism of the transplanted heart.", N. Engl. J. Med., Jan. 2002, 346(1), 5-15.

Rabbany et al, "Continuous delivery of stromal cell-derived factor-1 from alginate scaffolds accelerates wound healing", Cell Transplantation, 2010, 19(4), 399-408, E-publication Dec. 8, 2009.

Rosengart et al, "Angiogenesis gene therapy: Phase I assessment of direct intramyocardial administration of an adenovirus vector expressing VEGF121 cDNA to individuals with clinically significant severe coronary artery disease.", Circulation, Aug. 3, 1999, 100(5), 468-474.

Sasaki et al, "Autologous heart cell transplantation into myocardial scar tissue improves heart function.", J. Mol. Cell Cardiol., Mar. 1999, 31(3), 513-522.

Sasaki et al, "Cardiothoracic transplantation. Fetal cell transplantation: A comparison of three cell types.", J. Thorac. Cardiovac. Surg. Oct. 1999, 118(4), 715-725.

Sasaki et al, "Stromel cell-derived factor-1 (SDF-1) protects deterioration of cardiac function through angiogenesis after acute myocardial infarction (AMI) in mice", circulation Oct. 26, 2004, 110(17), 111, 77th scientific meeting of the American Heart Association, New Orleans, LA, Nov. 7-10, 2004, Abstract.

Schenk et al, "Monocyte chemotactic protein-3 is a myocardial mesenchymal stem cell homing factor", stem cells, Jan. 2007, 25(1), 245-251, e-publication Oct. 19, 2006.

Schuh et al, "Transplantation of endothelial progenitor cells improves neovascularization and left ventricular function after myocardial infarction in a rat model", Basic Res. Cardiol., Jan. 2008, 103(1), 69-77, Epublication Nov. 12, 2007.

Scorsin et al, "Comparison of the effects of fetal cardiomyocyte and skeletal myoblast transplantation on postinfarction left ventricular function.", J. Thorac. Cardiovasc. Surg., Jun. 2000, 119(6), 1169-1175.

Shake et al, Mesenchymal Stem Cell Implantation in a Swine Myocardial Infarct Model: Engraftment and Functional Effects, The Annals of Thoracic Surgical , Jun. 2002, 73(6), 1919-1925.

Simons et al, Pharmacological treatment of coronary artery disease with recombinant fibroblast growth factor-2: double-blind, randomized, controlled clinical trial., Circulation, Feb. 19, 2002, 105(7), 788-793.

Suzuki et al, "Cell transplantation for the treatment of acute myocardial infarction using vascular endothelial growth factor-expressing skeletal myoblasts.", Circulation, Sep. 18, 2001, 104(12 Suppl 1), 1207-1212.

Tachibana et al, The chemokine receptor CXCR4 is essential for vascularization of the gastrointestinal tract., Nature, Jun. 11, 1998, 393(6685), 591-594.

Tang, Mobilizing of haematopoietic stem cells to ischemic myocardium by plasmid mediated stromal-cell-derived factor-1α (SDF-1 α) treatment, Regulatory Peptides, Feb. 15, 2005, 125(1-3), 1-8.

Taylor et al, "Regenerating functional myocardium: Improved performance after skeletal myoblast transplantation.", Nat. Med. Aug. 1998, 4, 929-933.

Tomita et al, "Improved heart function with myogenesis and angiogenesis after autologous porcine bone marrow stromal cell transplantation.", J. Thorac. Cardiovascular Surg. Jun. 2002, 123(6), 1132-1140.

Topol, "Reperfusion therapy for acute myocardial infarction with fibrinolytic therapy or combination reduced fibrinolytic therapy and platelet glycoprotein IIB/IIIa Inhibition: The Gusto V Randomised Trial.", Lancet, Jun. 16, 2001, 357(9272), 1905-1914.

Udelson et al, "Therapeutic angiogenesis with recombinant fibroblast growth factor-2 improves stress and rest myocardial perfusion abnormalities in patients with severe symptomatic chronic coronary artery disease.", Circulation, Oct. 3, 2000, 102(14), 1605-1610.

Vale et al, "Randomized, single-blind, placebo-controlled pilot study of catheter-based myocardial gene transfer for therapeutic angiogenesis using left ventricular electromechanical mapping in patients with chronic myocardial ischemia.", circulation, May 1, 2001, 103(17), 2138-2143.

Wagers et al, "Little Evidence for Developmental plasticity of adult hematopoietic stem cells", Science, Sep. 2002, 297, 2256-2259.

Wright et al, "Hematopoietic stem cells are uniquely selective in their migratory response to chemokines", J. Exp. Med., May 6, 2002, 195(9), 1145-1154.

Yamaguchi et al, "Stromal Cell-Derived Factor-1 effects on Ex vivo expanded endothelial Progenitor Cell Recruitment for Ischemic Neovascularization", Circulation, Mar. 11, 2003, 107(9), 1322-1328.

Yano et al., "Stromel cell derived factor-1 (SDF-1)/CXCL12 attenuates diabetes in mice and promotes pancreatic beta-cell survival by activation of the prosurvival kinase Akt", Diabetes, Dec. 2007, 56(12), 2946-2957.

Yau et al, Enhanced myocardial angiogenesis by gene transfer with transplanted cells., Circulation, Sep. 18, 2001 104(12 Suppl 1), 1218-1222.

Yong et al, "Cord blood progenitor cells have greater transendothelial migratory activity and increased responses to SDF-1 and MIP-3beta compared with mobilized adult progenitor cells.", Br. J. Haematol., Nov. 1999, 107(2), 441-449.

Zhang et al, "Over-expression of CXCR4 on mesenchymal stem cells augments myoangiogenesis in the infarcted myocardium", J. Mol. Cell Cardiol., Feb. 2008, 44(2), 281-292, E-publication Dec. 7, 2007.

Zhang et al, SDF-1 expression by mesenchymal stem cells results in trophic support of cardiac myocytes after myocardial infarction, The FASEB Journal, Oct. 2007, 21(12), 3197-3207.

Zou et al, "Function of the chemokine receptor CXCR4 in haematopoiesis and in cerebellar development.", Jun. 11, 1998, Nature, 393(6685), 595-599.

* cited by examiner

SEQUENCE LISTING

```
<160> NUMBER OF SEQ ID NOS: 5

<210> SEQ ID NO 1
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Lys Pro Val Ser Leu Leu Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45
```

-continued

Val Cys Ile Asp Pro Lys Leu Lys Trp Ile Gln Glu Tyr Leu Glu Lys
        50                  55                  60

Ala Leu Asn Lys
65

<210> SEQ ID NO 2
<211> LENGTH: 89
<212> TYPE: PRT
<213> ORGANISM: Homo sapiens

<400> SEQUENCE: 2

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 3
<211> LENGTH: 89
<212> TYPE: PRT
<213> ORGANISM: Rattus norvegicus

<400> SEQUENCE: 3

Met Asp Ala Lys Val Val Ala Val Leu Ala Leu Val Leu Ala Ala Leu
1               5                   10                  15

Cys Ile Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Ser Asn Asn Arg Gln Val Cys Ile Asp Pro Lys Leu Lys Trp Ile Gln
65                  70                  75                  80

Glu Tyr Leu Asp Lys Ala Leu Asn Lys
                85

<210> SEQ ID NO 4
<211> LENGTH: 1940
<212> TYPE: DNA
<213> ORGANISM: Homo sapiens

<400> SEQUENCE: 4
gccgcacttt cactctccgt cagccgcatt gcccgctcgg cgtccggccc ccgacccgcg      60
ctcgtccgcc cgcccgcccg cccgcccgcg ccatgaacgc caaggtcgtg gtcgtgctgg     120
tcctcgtgct gaccgcgctc tgcctcagcg acgggaagcc cgtcagcctg agctacagat     180
gcccatgccg attcttcgaa agccatgttg ccagagccaa cgtcaagcat ctcaaaattc     240
tcaacactcc aaactgtgcc ttcagattgt agcccggct gaagaacaac aacagacaag     300
tgtgcattga cccgaagcta aagtggatta aggagtacct ggagaaagct ttaaacaagt     360
aagcacaaca gccaaaaagg actttccgct agacccactc gaggaaaact aaaaccttgt     420

```
gagagatgaa agggcaaaga cgtggggag ggggccttaa ccatgaggac caggtgtgtg      480
tgtggggtgg gcacattgat ctgggatcgg gcctgaggtt tgccagcatt tagaccctgc      540
atttatagca tacggtatga tattgcagct tatattcatc catgccctgt acctgtgcac      600
gttggaactt ttattactgg ggttttttcta agaaagaaat tgtattatca acagcatttt      660
caagcagtta gttccttcat gatcatcaca atcatcatca ttctcattct cattttttaa      720
atcaacgagt acttcaagat ctgaatttgg cttgtttgga gcatctcctc tgctcccctg      780
gggagtctgg gcacagtcag gtggtggctt aacagggagc tggaaaaagt gtcctttctt      840
cagacactga ggctcccgca gcagcgcccc tcccaagagg aaggcctctg tggcactcag      900
ataccgactg gggctgggcg ccgccactgc cttcacctcc tctttcaacc tcagtgattg      960
gctctgtggg ctccatgtag aagccactat tactgggact gtgctcagag acccctctcc     1020
cagctattcc tactctctcc ccgactccga gagcatgctt aatcttgctt ctgcttctca     1080
tttctgtagc ctgatcagcg ccgcaccagc cgggaagagg gtgattgctg gggctcgtgc     1140
cctgcatccc tctcctccca gggcctgccc cacagctcgg gccctctgtg agatccgtct     1200
ttggcctcct ccagaatgga gctggccctc tcctggggat gtgtaatggt cccctgctt      1260 acccgcaaaa gacaagtctt tacagaatca aatgcaattt taaatctgag agctcgcttt     1320
gagtgactgg gttttgtgat tgcctctgaa gcctatgtat gccatggagg cactaacaaa     1380
ctctgaggtt tccgaaatca gaagcgaaaa aatcagtgaa taaaccatca tcttgccact     1440
accccctcct gaagccacag cagggtttca ggttccaatc agaactgttg gcaaggtgac     1500
atttccatgc ataaatgcga tccacagaag gtcctggtgg tatttgtaac tttttgcaag     1560 gcatttttt atatatattt ttgtgcacat ttttttttac gtttctttag aaaacaaatg     1620
tatttcaaaa tatatttata gtcgaacaat tcatatattt gaagtggagc catatgaatg     1680
tcagtagttt atacttctct attatctcaa actactggca atttgtaaag aaatatatat     1740
gatatataaa tgtgattgca gcttttcaat gttagccaca gtgtattttt tcacttgtac     1800
taaaattgta tcaaatgtga cattatatgc actagcaata aaatgctaat tgtttcatgg     1860
tataaacgtc ctactgtatg tgggaattta tttacctgaa ataaaattca ttagttgtta     1920
gtgatggagc ttaaaaaaaa                                                 1940

<210> SEQ ID NO 5
<211> LENGTH: 293
<212> TYPE: DNA
<213> ORGANISM: Rattus norvegicus

<400> SEQUENCE: 5
ccatggacgc caaggtcgtc gctgtgctgg ccctggtgct ggccgcgctc tgcatcagtg       60
acggtaagcc agtcagcctg agctacagat gcccctgccg attctttgag agccatgtcg      120
ccagagccaa cgtcaaacat ctgaaaatcc tcaacactcc aaactgtgcc cttcagattg      180
ttgcaaggct gaaaagcaac aacagacaag tgtgcattga cccgaaatta aagtggatcc      240
aagagtacct ggacaaagcc ttaaacaagt aagcacaaca gcccaaagga ctt            293
```

SDF-1 DELIVERY FOR TREATING ISCHEMIC TISSUE

CROSS-REFERENCE TO RELATED APPLICATIONS

This application is a continuation of U.S. application Ser. No. 13/393,141, filed Jun. 7, 2012 as entry into the U.S. national stage of International Application No. PCT/US2010/047175, filed Aug. 30, 2010, which, in turn, claims priority from U.S. Provisional Application Nos. 61/237,775, filed Aug. 28, 2009, and 61/334,216, filed May 13, 2010. The subject matter of the foregoing applications is incorporated herein by reference in its entirety for all purposes.

SEQUENCE LISTING

The instant application contains a Sequence Listing which has been submitted in ASCII format via EFS-Web and is hereby incorporated by reference in its entirety. Said ASCII copy, created on Jul. 23, 2012, is named JUVE0078.txt and is 5,914 bytes in size.

FIELD OF THE INVENTION

This application relates to SDF-1 delivery methods and compositions for treating a cardiomyopathy and to the use of SDF-1 delivery methods and compositions for treating an ischemic cardiomyopathy.

BACKGROUND OF THE INVENTION

Ischemia is a condition wherein the blood flow is completely obstructed or considerably reduced in localized parts of the body, resulting in anoxia, reduced supply of substrates and accumulation of metabolites. Although the extent of ischemia depends on the acuteness of vascular obstruction, its duration, tissue sensitivity to it, and developmental extent of collateral vessels, dysfunction usually occurs in ischemic organs or tissues, and prolonged ischemia results in atrophy, denaturation, apoptosis, and necrosis of affected tissues.

In ischemic cardiomyopathy, which are diseases that affect the coronary artery and cause myocardial ischemia, the extent of ischemic myocardial cell injury proceeds from reversible cell damage to irreversible cell damage with increasing time of the coronary artery obstruction.

SUMMARY OF THE INVENTION

This application relates to a method of treating a cardiomyopathy in a subject. The cardiomyopathy can include, for example, cardiomyopathies associated with a pulmonary embolus, a venous thrombosis, a myocardial infarction, a transient ischemic attack, a peripheral vascular disorder, atherosclerosis, and/or other myocardial injury or vascular disease. The method includes administering directly to or expressing locally in a weakened, ischemic, and/or peri-infarct region of myocardial tissue of the subject an amount of SDF-1 effective to cause functional improvement in at least one of the following parameters: left ventricular volume, left ventricular area, left ventricular dimension, cardiac function, 6-minute walk test (6MWT), or New York Heart Association (NYHA) functional classification.

In an aspect of the application, the amount of SDF-1 administered to the weakened, ischemic, and/or peri-infarct region is effective to cause functional improvement in at least one of left ventricular end systolic volume, left ventricular ejection fraction, wall motion score index, left ventricular end diastolic length, left ventricular end systolic length, left ventricular end diastolic area, left ventricular end systolic area, left ventricular end diastolic volume, 6-minute walk test (6MWT), or New York Heart Association (NYHA) functional classification. In another aspect of the application, the amount of SDF-1 administered to the weakened, ischemic, and/or peri-infarct region is effective to improve left ventricular end systolic volume. In a further aspect of the application, the amount of SDF-1 administered to the weakened, ischemic, and/or peri-infarct region is effective to improve left ventricular ejection fraction.

In some aspects of the application, the amount of SDF-1 administered to the weakened, ischemic, and/or peri-infarct region is effective to improve left ventricular end systolic volume by at least about 10%. In other aspects of the application, the amount of SDF-1 administered to the weakened, ischemic, and/or peri-infarct region is effective to improve left ventricular end systolic volume by at least about 15%. In still further aspects of the application, the amount of SDF-1 administered to the weakened, ischemic, and/or peri-infarct region is effective to improve left ventricular end systolic volume by at least about 10%, improve left ventricular ejection fraction by at least about 10%, improve wall motion score index by at least about 5%, improve six minute walk distance at least about 30 meters, and improve NYHA class by at least 1 class. In a further aspect of the application, the amount of SDF-1 administered to the weakened, ischemic, and/or peri-infarct region is effective to improve left ventricular ejection fraction by at least about 10%.

In another aspect of the application, the amount of SDF-1 administered to the weakened, ischemic, and/or peri-infarct region is effective to substantially improve vasculogenesis of the weakened, ischemic, and/or peri-infarct region by at least about 20% based on vessel density or measured by myocardial perfusion imaging (e.g., SPECT or PET) with an improvement in summed rest score, summed stress score, and/or summed difference score of at least about 10%. The SDF-1 can be administered by injecting a solution comprising SDF-1 expressing plasmid in the weakened, ischemic, and/or peri-infarct region and expressing SDF-1 from the weakened, ischemic, and/or peri-infarct region. The SDF-1 can be expressed from the weakened, ischemic, and/or peri-infarct region at an amount effective to improve left ventricular end systolic volume.

In an aspect of the application, the SDF-1 plasmid can be administered to the weakened, ischemic, and/or peri-infarct region in multiple injections of the solution with each injection comprising about 0.33 mg/ml to about 5 mg/ml of SDF-1 plasmid solution. In one example, the SDF-1 plasmid can be administered to the weakened, ischemic, and/or peri-infarct region in at least about 10 injections. Each injection administered to the weakened, ischemic, and/or peri-infarct region can have a volume of at least about 0.2 ml. The SDF-1 can be expressed in the weakened, ischemic, and/or peri-infarct region for greater than about three days.

In an example application, each injection of solution comprising SDF-1 expressing plasmid can have an injection volume of at least about 0.2 ml and an SDF-1 plasmid concentration per injection of about 0.33 mg/ml to about 5 mg/ml. In another aspect of the application, at least one functional parameter of the of the heart can be improved by injecting the SDF-1 plasmid into the weakened, ischemic, and/or peri-infarct region of the heart at an injection volume per site of at least about 0.2 ml, in at least about 10 injection sites, and at an SDF-1 plasmid concentration per injection of about 0.33 mg/ml to about 5 mg/ml.

In a further example, the amount of SDF-1 plasmid administered to the weakened, ischemic, and/or peri-infarct region that can improve at least one functional parameter of the heart is greater than about 4 mg. The volume of solution of SDF-1 plasmid administered to the weakened, ischemic, and/or peri-infarct region that can improve at least one functional parameter of the heart is at least about 10 ml.

In another aspect of the application, the subject to which the SDF-1 is administered can be a large mammal, such as a human or pig. The SDF-1 plasmid can be administered to the subject by catheterization, such as intra-coronary catheterization or endo-ventricular catheterization. The myocardial tissue of the subject can be imaged to define the area of weakened, ischemic, and/or peri-infarct region prior to administration of the SDF-1 plasmid, and the SDF-1 plasmid can be administered to the weakened, ischemic, and/or peri-infarct region defined by the imaging. The imaging can include at least one of echocardiography, magnetic resonance imaging, coronary angiogram, electroanatomical mapping, or fluoroscopy.

The application also relates to a method of treating a myocardial infarction in a large mammal by administering SDF-1 plasmid to the peri-infarct region of the myocardium of the mammal by catheterization, such as intra-coronary catheterization or endo-ventricular catheterization. The SDF-1 administered by catheterization can be expressed from the peri-infarct region at an amount effective to cause functional improvement in at least one of the following parameters: left ventricular volume, left ventricular area, left ventricular dimension, cardiac function, 6-minute walk test (6MWT), or New York Heart Association (NYHA) functional classification.

In an aspect of the application, the amount of SDF-1 administered to the peri-infarct region is effective to cause functional improvement in at least one of left ventricular end systolic volume, left ventricular ejection fraction, wall motion score index, left ventricular end diastolic length, left ventricular end systolic length, left ventricular end diastolic area, left ventricular end systolic area, left ventricular end diastolic volume, 6-minute walk test (6MWT), or New York Heart Association (NYHA) functional classification. In another aspect of the application, the amount of SDF-1 administered to the peri-infarct region is effective to improve left ventricular end systolic volume. In a further aspect of the application, the amount of SDF-1 administered to the weakened, ischemic, and/or peri-infarct region is effective to improve left ventricular ejection fraction.

In some aspects of the application, the amount of SDF-1 administered to the peri-infarct region is effective to improve left ventricular end systolic volume by at least about 10%. In other aspects of the application, the amount of SDF-1 administered to the peri-infarct region is effective to improve left ventricular end systolic volume by at least about 15%. In still further aspects of the application, the amount of SDF-1 administered to the peri-infarct region is effective to improve left ventricular end systolic volume by at least about 10%, improve left ventricular ejection fraction by at least about 10%, improve wall motion score index by about 5%, improve six minute walk distance at least about 30 meters, or improve NYHA class by at least 1 class. In a further aspect of the application, the amount of SDF-1 administered to the weakened, ischemic, and/or peri-infarct region is effective to improve left ventricular ejection fraction by at least about 10%.

In another aspect of the application, the amount of SDF-1 administered to the peri-infarct region is effective to substantially improve vasculogenesis of the peri-infarct region by at least about 20% based on vessel density.

In an aspect of the application, the SDF-1 plasmid can be administered to the weakened, ischemic, and/or peri-infarct region in multiple injections of the solution with each injection comprising about 0.33 mg/ml to about 5 mg/ml of SDF-1 plasmid/solution. In one example, the SDF-1 plasmid can be administered to the weakened, ischemic, and/or peri-infarct region in at least about 10 injections. Each injection administered to the weakened, ischemic, and/or peri-infarct region can have a volume of at least about 0.2 ml. The SDF-1 can be expressed in the weakened, ischemic, and/or peri-infarct region for greater than about three days.

In an example application, each injection of solution comprising SDF-1 expressing plasmid can have an injection volume of at least about 0.2 ml and an SDF-1 plasmid concentration per injection of about 0.33 mg/ml to about 5 mg/ml. In another aspect of the application, at least one functional parameter of the of the heart can be improved by injecting the SDF-1 plasmid into the weakened, ischemic, and/or peri-infarct region of the heart at an injection volume per site of at least about 0.2 ml, in at least about 10 injection sites, and at an SDF-1 plasmid concentration per injection of about 0.33 mg/ml to about 5 mg/ml.

In a further example, the amount of SDF-1 plasmid administered to the weakened, ischemic, and/or peri-infarct region that can improve at least one functional parameter of the heart is greater than about 4 mg. The volume of solution of SDF-1 plasmid administered to the weakened, ischemic, and/or peri-infarct region that can improve at least one functional parameter of the heart is at least about 10 ml.

The application further relates to a method of improving left ventricular end systolic volume in a large mammal after myocardial infarction. The method includes administering SDF-1 plasmid to the peri-infarct region of the mammal by endo-ventricular catheterization. The SDF-1 can be expressed from the peri-infarct region at an amount effective to cause functional improvement in left ventricular end systolic volume.

In some aspects of the application, the amount of SDF-1 administered to the peri-infarct region is effective to improve left ventricular end systolic volume by at least about 10%. In other aspects of the application, the amount of SDF-1 administered to the peri-infarct region is effective to improve left ventricular end systolic volume by at least about 15%. In still further aspects of the application, the amount of SDF-1 administered to the peri-infarct region is effective to improve left ventricular end systolic volume by at least about 10%, improve left ventricular ejection fraction by at least about 10%, improve wall motion score index by about 5%, improve six minute walk distance at least about 30 meters, or improve NYHA class by at least 1 class.

In an aspect of the application, the SDF-1 plasmid can be administered to the weakened, ischemic, and/or peri-infarct region in multiple injections of the solution with each injection comprising about 0.33 mg/ml to about 5 mg/ml of SDF-1 plasmid/solution. In one example, the SDF-1 plasmid can be administered to the weakened, ischemic, and/or peri-infarct region in at least about 10 injections. Each injection administered to the weakened, ischemic, and/or peri-infarct region can have a volume of at least about 0.2 ml. The SDF-1 can be expressed in the weakened, ischemic, and/or peri-infarct region for greater than about three days.

In an example application, each injection of solution comprising SDF-1 expressing plasmid can have an injection volume of at least about 0.2 ml and an SDF-1 plasmid concentration per injection of about 0.33 mg/ml to about 5 mg/ml. In another aspect of the application, left ventricular end systolic volume of the of the heart can be improved can be improved at about 10% by injecting the SDF-1 plasmid into the weakened, ischemic, and/or peri-infarct region of the heart at an injection volume per site of at least about 0.2 ml, in at least about 10 injection sites, and at an SDF-1 plasmid concentration per injection of about 0.33 mg/ml to about 5 mg/ml.

In a further example, the amount of SDF-1 plasmid administered to the weakened, ischemic, and/or peri-infarct region that can improve left ventricular end systolic volume is greater than about 4 mg. The volume of solution of SDF-1 plasmid administered to the weakened, ischemic, and/or peri-infarct region that can improve left ventricular end systolic volume of the heart is at least about 10 ml.

BRIEF DESCRIPTION OF THE DRAWINGS

The foregoing and other features of the application will become apparent to those skilled in the art to which the application relates upon reading the following description with reference to the accompanying drawings.

DETAILED DESCRIPTION

Figure 1:
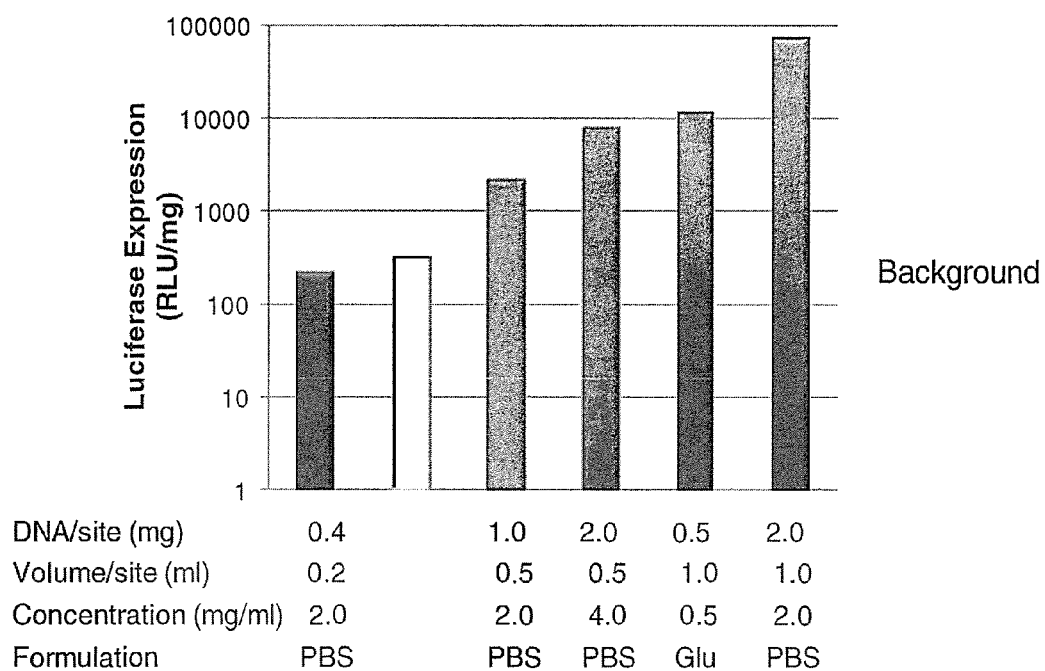
FIG. 1 is a chart illustrating luciferase expression for varying amounts and volume of DNA in a porcine model.

Unless defined otherwise, all technical and scientific terms used herein have the same meaning as is commonly understood by one of skill in the art to which the application(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail.

Unless otherwise defined, all technical terms used herein have the same meaning as commonly understood by one of ordinary skill in the art to which this application belongs. Commonly understood definitions of molecular biology terms can be found in, for example, Rieger et al., Glossary of Genetics: Classical and Molecular, 5th edition, Springer-Verlag: New York, 1991; and Lewin, Genes V, Oxford University Press: New York, 1994.

Methods involving conventional molecular biology techniques are described herein. Such techniques are generally known in the art and are described in detail in methodology treatises, such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the application. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

Where reference is made to a URL or other such identifier or address, it understood that such identifiers can change and particular information on the internet can come and go, but equivalent information can be found by searching the internet. Reference thereto evidences the availability and public dissemination of such information.

As used herein, "nucleic acid" refers to a polynucleotide containing at least two covalently linked nucleotide or nucleotide analog subunits. A nucleic acid can be a deoxyribonucleic acid (DNA), a ribonucleic acid (RNA), or an analog of DNA or RNA. Nucleotide analogs are commercially available and methods of preparing polynucleotides containing such nucleotide analogs are known (Lin et al. (1994) Nucl. Acids Res. 22:5220-5234; Jellinek et al. (1995) Biochemistry 34:11363-11372; Pagratis et al. (1997) Nature Biotechnol. 15:68-73). The nucleic acid can be single-stranded, double-stranded, or a mixture thereof. For purposes herein, unless specified otherwise, the nucleic acid is double-stranded, or it is apparent from the context.

As used herein, "DNA" is meant to include all types and sizes of DNA molecules including cDNA, plasmids and DNA including modified nucleotides and nucleotide analogs.

As used herein, "nucleotides" include nucleoside mono-, di-, and triphosphates. Nucleotides also include modified nucleotides, such as, but are not limited to, phosphorothioate nucleotides and deazapurine nucleotides and other nucleotide analogs.

As used herein, the term "subject" or "patient" refers to animals into which the large DNA molecules can be introduced. Included are higher organisms, such as mammals and birds, including humans, primates, rodents, cattle, pigs, rabbits, goats, sheep, mice, rats, guinea pigs, cats, dogs, horses, chicken and others.

As used herein "large mammal" refers to mammals having a typical adult weight of at least 10 kg. Such large mammals can include, for example, humans, primates, dogs, pigs, cattle and is meant to exclude smaller mammals, such as mice, rats, guinea pigs, and other rodents.

As used herein, "administering to a subject" is a procedure by which one or more delivery agents and/or large nucleic acid molecules, together or separately, are introduced into or applied onto a subject such that target cells which are present in the subject are eventually contacted with the agent and/or the large nucleic acid molecules.

As used herein, "delivery," which is used interchangeably with "transduction," refers to the process by which exogenous nucleic acid molecules are transferred into a cell such that they are located inside the cell. Delivery of nucleic acids is a distinct process from expression of nucleic acids.

As used herein, a "multiple cloning site (MCS)" is a nucleic acid region in a plasmid that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector.

As used herein, "origin of replication" (often termed "ori"), is a specific nucleic acid sequence at which replication is initiated. Alternatively, an autonomously replicating sequence (ARS) can be employed if the host cell is yeast.

As used herein, "selectable or screenable markers" confer an identifiable change to a cell permitting easy identification of cells containing an expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al., Virology 52:456 (1973); Sambrook et al., Molecular Cloning: A Laboratory Manual (1989); Davis et al., Basic Methods in Molecular Biology (1986); Chu et al., Gene 13:197 (1981). Such techniques can be used to introduce one or more exogenous DNA moieties, such as a nucleotide integration vector and other nucleic acid molecules, into suitable host cells. The term captures chemical, electrical, and viral-mediated transfection procedures.

As used herein, "expression" refers to the process by which nucleic acid is translated into peptides or is transcribed into RNA, which, for example, can be translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

As used herein, "genetic therapy" involves the transfer of heterologous DNA to cells of a mammal, particularly a human, with a disorder or conditions for which therapy or diagnosis is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product; it may encode a product, such as a peptide or RNA that in some manner mediates, directly or indirectly, expression of a therapeutic product. Genetic therapy may also be used to deliver nucleic acid encoding a gene product to replace a defective gene or supplement a gene product produced by the mammal or the cell in which it is introduced. The introduced nucleic acid may encode a therapeutic compound, such as a growth factor inhibitor thereof, or a tumor necrosis factor or inhibitor thereof, such as a receptor therefore, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof.

As used herein, "heterologous nucleic acid sequence" is typically DNA that encodes RNA and proteins that are not normally produced in vivo by the cell in which it is expressed or that mediates or encodes mediators that alter expression of endogenous DNA by affecting transcription, translation, or other regulatable biochemical processes. A heterologous nucleic acid sequence may also be referred to as foreign DNA. Any DNA that one of skill in the art would recognize or consider as heterologous or foreign to the cell in which it is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

As used herein the term "cardiomyopathy" refers to the deterioration of the function of the myocardium (i.e., the actual heart muscle) for any reason. Subjects with cardiomyopathy are often at risk of arrhythmia, sudden cardiac death, or hospitalization or death due to heart failure.

As used herein, the term "ischemic cardiomyopathy" is a weakness in the muscle of the heart due to inadequate oxygen delivery to the myocardium with coronary artery disease being the most common cause.

As used herein the term "ischemic cardiac disease" refers to any condition in which heart muscle is damaged or works inefficiently because of an absence or relative deficiency of its blood supply; most often caused by atherosclerosis, it includes angina pectoris, acute myocardial infarction, chronic ischemic heart disease, and sudden death.

As used herein the term "myocardial infarction" refers to the damaging or death of an area of the heart muscle (myocardium) resulting from a blocked blood supply to that area.

As used herein the term "6-minute walk test" or "6MWT" refers to a test that measures the distance that a patient can quickly walk on a flat, hard surface in a period of 6 minutes (the 6MWD). It evaluates the global and integrated responses of all the systems involved during exercise, including the pulmonary and cardiovascular systems, systemic circulation, peripheral circulation, blood, neuromuscular units, and muscle metabolism. It does not provide specific information on the function of each of the different organs and systems involved in exercise or the mechanism of exercise limitation, as is possible with maximal cardiopulmonary exercise testing. The self-paced 6MWT assesses the submaximal level of functional capacity. (See for example, AM J Respir Crit. Care Med, Vol. 166. Pp 111-117 (2002))

As used herein "New York Heart Association (NYHA) functional classification" refers to a classification for the extent of heart failure. It places patients in one of four categories based on how much they are limited during physical activity; the limitations/symptoms are in regards to normal breathing and varying degrees in shortness of breath and or angina pain:

| NYHA Class | Symptoms |
| --- | --- |
| I | No symptoms and no limitation in ordinary physical activity, e.g. shortness of breath when walking, climbing stairs etc. |
| II | Mild symptoms (mild shortness of breath and/or angina) and slight limitation during ordinary activity. |
| III | Marked limitation in activity due to symptoms, even during less-than-ordinary activity, e.g. walking short distances (20-100 m). Comfortable only at rest. |
| IV | Severe limitations. Experiences symptoms even while at rest. Mostly bedbound patients. |

This application relates to compositions and methods of treating a cardiomyopathy in a subject that results in reduced and/or impaired myocardial function. The cardiomyopathy treated by the compositions and methods herein can include cardiomyopathies associated with a pulmonary embolus, a venous thrombosis, a myocardial infarction, a transient ischemic attack, a peripheral vascular disorder, atherosclerosis, ischemic cardiac disease and/or other myocardial injury or vascular disease. The method of treating the cardiomyopathy can include locally administering (or locally delivering) to weakened myocardial tissue, ischemic myocardial tissue, and/or apoptotic myocardial tissue, such as the peri-infarct region of a heart following myocardial infarction, an amount of stromal-cell derived factor-1 (SDF-1) that is effective to cause functional improvement in at least one of the following parameters: left ventricular volume, left ventricular area, left ventricular dimension, cardiac function, 6-minute walk test (6MWT), or New York Heart Association (NYHA) functional classification.

It was found using a porcine model of heart failure that mimics heart failure in a human that functional improvement of ischemic myocardial tissue is dependent on the amount, dose, and/or delivery of SDF-1 administered to the ischemic myocardial tissue and that the amount, dose, and/or delivery of SDF-1 to the ischemic myocardial tissue can be optimized so that myocardial functional parameters, such as left ventricular volume, left ventricular area, left ventricular dimension, or cardiac function are substantially improved. As discussed below, in some aspects, the amount, concentration, and volume of SDF-1administerd to the ischemic myocardial tissue can be controlled and/or optimized to substantially improve the functional parameters (e.g., left ventricular volume, left ventricular area, left ventricular dimension, cardiac function, 6-minute walk test (6MWT), and/or New York Heart Association (NYHA) functional classification) while mitigating adverse side effects.

In one example, the SDF-1 can be administered directly or locally to a weakened region, an ischemic region, and/or peri-infarct region of myocardial tissue of a large mammal (e.g., pig or human) in which there is a deterioration or worsening of a functional parameter of the heart, such as left ventricular volume, left ventricular area, left ventricular dimension, or cardiac function as a result of an ischemic cardiomyopathy, such as a myocardial infarction. The deterioration or worsening of the functional parameter can include, for example, an increase in left ventricular end systolic volume, decrease in left ventricular ejection fraction, increase in wall motion score index, increase in left ventricular end diastolic length, increase in left ventricular end systolic length, increase in left ventricular end diastolic area (e.g., mitral valve level and papillary muscle insertion level), increase in left ventricular end systolic area (e.g., mitral valve level and papillary muscle insertion level), or increase in left ventricular end diastolic volume as measured using, for example, using echocardiography.

In an aspect of the application, the amount of SDF-1 administered to the weakened region, ischemic region, and/or peri-infarct region of the myocardial tissue of the large mammal can be an amount effective to improve at least one functional parameter of the myocardium, such as a decrease in left ventricular end systolic volume, increase in left ventricular ejection fraction, decrease in wall motion score index, decrease in left ventricular end diastolic length, decrease in left ventricular end systolic length, decrease in left ventricular end diastolic area (e.g., mitral valve level and papillary muscle insertion level), decrease in left ventricular end systolic area (e.g., mitral valve level and papillary muscle insertion level), or decrease in left ventricular end diastolic volume measured using, for example, using echocardiography as well as improve the subject's 6-minute walk test (6MWT) or New York Heart Association (NYHA) functional classification.

In another aspect of the application, the amount of SDF-1 administered to the weakened region, ischemic region, and/or peri-infarct region of the myocardial tissue of the large mammal with a cardiomyopathy is effective to improve left ventricular end systolic volume in the mammal by at least about 10%, and more specifically at least about 15%, after 30 days following administration as measured by echocardiography. The percent improvement is relative to each subject treated and is based on the respective parameter measured prior to or at the time of therapeutic intervention or treatment.

In a further aspect of the application, the amount of SDF-1 administered to the weakened region, ischemic region, and/or peri-infarct region of the myocardial tissue of the large mammal with a cardiomyopathy is effective to improve left ventricular end systolic volume by at least about 10%, improve left ventricular ejection fraction by at least about 10%, and improve wall motion score index by about 5%, after 30 days following administration as measured by echocardiography.

In a still further aspect of the application, the amount of SDF-1 administered to the weakened region, ischemic region, and/or peri-infarct region of the myocardial tissue of the large mammal with a cardiomyopathy is effective to improve vasculogenesis of the weakened region, ischemic region, and/or peri-infarct region by at least 20% based on vessel density or an increase in cardiac perfusion measured by SPECT imaging. A 20% improvement in vasculogenesis has been shown to be clinically significant (Losordo Circulation 2002; 105: 2012).

In a still further aspect of the application, the amount of SDF-1 administered to the weakened region, ischemic region, and/or peri-infarct region of the myocardial tissue of the large mammal with a cardiomyopathy is effective to improve six minute walk distance at least about 30 meters or improve NYHA class by at least 1 class.

The SDF-1 described herein can be administered to the weakened region, the ischemic region, and/or peri-infarct region of the myocardial tissue following tissue injury (e.g., myocardial infarction) to about hours, days, weeks, or months after onset of down-regulation of SDF-1. The period of time that the SDF-1 is administered to the cells can comprise from about immediately after onset of the cardiomyopathy (e.g., myocardial infarction) to about days, weeks, or months after the onset of the ischemic disorder or tissue injury.

SDF-1 in accordance with the application that is administered to the weakened, ischemic, and/or a peri-infarct region of the myocardial tissue peri-infarct region can have an amino acid sequence that is substantially similar to a native mammalian SDF-1 amino acid sequence. The amino acid sequence of a number of different mammalian SDF-1 protein are known including human, mouse, and rat. The human and rat SDF-1 amino acid sequences are at least about 92% identical (e.g., about 97% identical). SDF-1 can comprise two isoforms, SDF-1 alpha and SDF-1 beta, both of which are referred to herein as SDF-1 unless identified otherwise.

The SDF-1 can have an amino acid sequence substantially identical to SEQ ID NO: 1. The SDF-1 that is over-expressed can also have an amino acid sequence substantially similar to one of the foregoing mammalian SDF-1 proteins. For example, the SDF-1 that is over-expressed can have an amino acid sequence substantially similar to SEQ ID NO: 2. SEQ ID NO: 2, which substantially comprises SEQ ID NO: 1, is the amino acid sequence for human SDF-1 and is identified by GenBank Accession No. NP954637. The SDF-1 that is over-expressed can also have an amino acid sequence that is substantially identical to SEQ ID NO: 3. SEQ ID NO: 3 includes the amino acid sequences for rat SDF and is identified by GenBank Accession No. AAF01066.

The SDF-1 in accordance with the application can also be a variant of mammalian SDF-1, such as a fragment, analog and derivative of mammalian SDF-1. Such variants include, for example, a polypeptide encoded by a naturally occurring allelic variant of native SDF-1 gene (i.e., a naturally occurring nucleic acid that encodes a naturally occurring mammalian SDF-1 polypeptide), a polypeptide encoded by an alternative splice form of a native SDF-1 gene, a polypeptide encoded by a homolog or ortholog of a native SDF-1 gene, and a polypeptide encoded by a non-naturally occurring variant of a native SDF-1 gene.

SDF-1 variants have a peptide sequence that differs from a native SDF-1 polypeptide in one or more amino acids. The peptide sequence of such variants can feature a deletion, addition, or substitution of one or more amino acids of a SDF-1 variant. Amino acid insertions are preferably of about 1 to 4 contiguous amino acids, and deletions are preferably of about 1 to 10 contiguous amino acids. Variant SDF-1 polypeptides substantially maintain a native SDF-1 functional activity. Examples of SDF-1 polypeptide variants can be made by expressing nucleic acid molecules that feature silent or conservative changes. One example of an SDF-1 variant is listed in U.S. Pat. No. 7,405,195, which is herein incorporated by reference in its entirety.

SDF-1 polypeptide fragments corresponding to one or more particular motifs and/or domains or to arbitrary sizes, are within the scope of this application. Isolated peptidyl portions of SDF-1 can be obtained by screening peptides recombinantly produced from the corresponding fragment of the nucleic acid encoding such peptides. For example, an SDF-1 polypeptide may be arbitrarily divided into fragments of desired length with no overlap of the fragments, or preferably divided into overlapping fragments of a desired length. The fragments can be produced recombinantly and tested to identify those peptidyl fragments, which can function as agonists of native CXCR-4 polypeptides.

Variants of SDF-1 polypeptides can also include recombinant forms of the SDF-1 polypeptides. Recombinant polypeptides in some embodiments, in addition to SDF-1 polypeptides, are encoded by a nucleic acid that can have at least 70% sequence identity with the nucleic acid sequence of a gene encoding a mammalian SDF-1.

SDF-1 variants can include agonistic forms of the protein that constitutively express the functional activities of native SDF-1. Other SDF-1 variants can include those that are resistant to proteolytic cleavage, as for example, due to mutations, which alter protease target sequences. Whether a change in the amino acid sequence of a peptide results in a variant having one or more functional activities of a native SDF-1 can be readily determined by testing the variant for a native SDF-1 functional activity.

The SDF-1 nucleic acid that encodes the SDF-1 protein can be a native or non-native nucleic acid and be in the form of RNA or in the form of DNA (e.g., cDNA, genomic DNA, and synthetic DNA). The DNA can be double-stranded or single-stranded, and if single-stranded may be the coding (sense) strand or non-coding (anti-sense) strand. The nucleic acid coding sequence that encodes SDF-1 may be substantially similar to a nucleotide sequence of the SDF-1 gene, such as nucleotide sequence shown in SEQ ID NO: 4 and SEQ ID NO: 5. SEQ ID NO: 4 and SEQ ID NO: 5 comprise, respectively, the nucleic acid sequences for human SDF-1 and rat SDF-1 and are substantially similar to the nucleic sequences of GenBank Accession No. NM199168 and GenBank Accession No. AF189724. The nucleic acid coding sequence for SDF-1 can also be a different coding sequence which, as a result of the redundancy or degeneracy of the genetic code, encodes the same polypeptide as SEQ ID NO: 1, SEQ ID NO: 2, and SEQ ID NO: 3.

Other nucleic acid molecules that encode SDF-1 are variants of a native SDF-1, such as those that encode fragments, analogs and derivatives of native SDF-1. Such variants may be, for example, a naturally occurring allelic variant of a native SDF-1 gene, a homolog or ortholog of a native SDF-1 gene, or a non-naturally occurring variant of a native SDF-1 gene. These variants have a nucleotide sequence that differs from a native SDF-1 gene in one or more bases. For example, the nucleotide sequence of such variants can feature a deletion, addition, or substitution of one or more nucleotides of a native SDF-1 gene. Nucleic acid insertions are preferably of about 1 to 10 contiguous nucleotides, and deletions are preferably of about 1 to 10 contiguous nucleotides.

In other applications, variant SDF-1 displaying substantial changes in structure can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue (e.g., serine or threonine), for (or by) a hydrophobic residue (e.g., leucine, isoleucine, phenylalanine, valine or alanine); (b) a cysteine or proline for (or by) any other residue; (c) a residue having an electropositive side chain (e.g., lysine, arginine, or histidine), for (or by) an electronegative residue (e.g., glutamine or aspartine); or (d) a residue having a bulky side chain (e.g., phenylalanine), for (or by) one not having a side chain, (e.g., glycine).

Naturally occurring allelic variants of a native SDF-1 gene are nucleic acids isolated from mammalian tissue that have at least 70% sequence identity with a native SDF-1 gene, and encode polypeptides having structural similarity to a native SDF-1 polypeptide. Homologs of a native SDF-1 gene are nucleic acids isolated from other species that have at least 70% sequence identity with the native gene, and encode polypeptides having structural similarity to a native SDF-1 polypeptide. Public and/or proprietary nucleic acid databases can be searched to identify other nucleic acid molecules having a high percent (e.g., 70% or more) sequence identity to a native SDF-1 gene.

Non-naturally occurring SDF-1 gene variants are nucleic acids that do not occur in nature (e.g., are made by the hand of man), have at least 70% sequence identity with a native SDF-1 gene, and encode polypeptides having structural similarity to a native SDF-1 polypeptide. Examples of non-naturally occurring SDF-1 gene variants are those that encode a fragment of a native SDF-1 protein, those that hybridize to a native SDF-1 gene or a complement of to a native SDF-1 gene under stringent conditions, and those that share at least 65% sequence identity with a native SDF-1 gene or a complement of a native SDF-1 gene.

Nucleic acids encoding fragments of a native SDF-1 gene in some embodiments are those that encode amino acid residues of native SDF-1. Shorter oligonucleotides that encode or hybridize with nucleic acids that encode fragments of native SDF-1 can be used as probes, primers, or antisense molecules. Longer polynucleotides that encode or hybridize with nucleic acids that encode fragments of a native SDF-1 can also be used in various aspects of the application. Nucleic acids encoding fragments of a native SDF-1 can be made by enzymatic digestion (e.g., using a restriction enzyme) or chemical degradation of the full-length native SDF-1 gene or variants thereof.

Nucleic acids that hybridize under stringent conditions to one of the foregoing nucleic acids can also be used herein. For example, such nucleic acids can be those that hybridize to one of the foregoing nucleic acids under low stringency conditions, moderate stringency conditions, or high stringency conditions.

Nucleic acid molecules encoding a SDF-1 fusion protein may also be used in some embodiments. Such nucleic acids can be made by preparing a construct (e.g., an expression vector) that expresses a SDF-1 fusion protein when introduced into a suitable target cell. For example, such a construct can be made by ligating a first polynucleotide encoding a SDF-1 protein fused in frame with a second polynucleotide encoding another protein such that expression of the construct in a suitable expression system yields a fusion protein.

The nucleic acids encoding SDF-1 can be modified at the base moiety, sugar moiety, or phosphate backbone, for example, to improve stability of the molecule, hybridization, etc. The nucleic acids described herein may additionally include other appended groups such as peptides (e.g., for targeting target cell receptors in vivo), or agents facilitating transport across the cell membrane, hybridization-triggered cleavage. To this end, the nucleic acids may be conjugated to another molecule, (e.g., a peptide), hybridization triggered cross-linking agent, transport agent, hybridization-triggered cleavage agent, etc.

The SDF-1 can be delivered to the weakened, ischemic, and/or peri-infarct region of the myocardial tissue by administering an SDF-1 protein to the to the weakened, ischemic, and/or peri-infarct region, or by introducing an agent into cells of the weakened region, ischemic region, and/or peri-infarct region of the myocardial tissue that causes, increases, and/or upregulates expression of SDF-1 (i.e., SDF-1 agent). The SDF-1 protein expressed from the cells can be an expression product of a genetically modified cell.

The agent that causes, increases, and/or upregulates expression of SDF-1 can comprise natural or synthetic nucleic acids as described herein that are incorporated into recombinant nucleic acid constructs, typically DNA constructs, capable of introduction into and replication in the cells of the myocardial tissue. Such a construct can include a replication system and sequences that are capable of transcription and translation of a polypeptide-encoding sequence in a given cell.

One method of introducing the agent into a target cell involves using gene therapy. Gene therapy in some embodiments of the application can be used to express SDF-1 protein from a cell of the weakened region, ischemic region, and/or peri-infarct region of the myocardial tissue in vivo.

In an aspect of the application, the gene therapy can use a vector including a nucleotide encoding an SDF-1 protein. A "vector" (sometimes referred to as gene delivery or gene transfer "vehicle") refers to a macromolecule or complex of molecules comprising a polynucleotide to be delivered to a target cell, either in vitro or in vivo. The polynucleotide to be delivered may comprise a coding sequence of interest in gene therapy. Vectors include, for example, viral vectors (such as adenoviruses ('Ad'), adeno-associated viruses (AAV), and retroviruses), non-viral vectors, liposomes, and other lipid-containing complexes, and other macromolecular complexes capable of mediating delivery of a polynucleotide to a target cell.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available.

Vectors for use herein include viral vectors, lipid based vectors and other non-viral vectors that are capable of delivering a nucleotide to the cells of weakened region, ischemic region, and/or peri-infarct region of the myocardial tissue. The vector can be a targeted vector, especially a targeted vector that preferentially binds to the cells of weakened region, ischemic region, and/or peri-infarct region of the myocardial tissue. Viral vectors for use in the methods herein can include those that exhibit low toxicity to the cells of weakened region, ischemic region, and/or peri-infarct region of the myocardial tissue and induce production of therapeutically useful quantities of SDF-1 protein in a tissue-specific manner.

Examples of viral vectors are those derived from adenovirus (Ad) or adeno-associated virus (AAV). Both human and non-human viral vectors can be used and the recombinant viral vector can be replication-defective in humans. Where the vector is an adenovirus, the vector can comprise a polynucleotide having a promoter operably linked to a gene encoding the SDF-1 protein and is replication-defective in humans.

Other viral vectors that can be use in accordance with method of the application include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid.

Retroviruses, such as C-type retroviruses and lentiviruses, might also be used in some embodiments of the application. For example, retroviral vectors may be based on murine leukemia virus (MLV). See, e.g., Hu and Pathak, Pharmacol. Rev. 52:493-511, 2000 and Fong et al., Crit. Rev. Ther. Drug Carrier Syst. 17:1-60, 2000. MLV-based vectors may contain up to 8 kb of heterologous (therapeutic) DNA in place of the viral genes. The heterologous DNA may include a tissue-specific promoter and an SDF-1 nucleic acid. In methods of delivery to cells proximate the wound, it may also encode a ligand to a tissue specific receptor.

Additional retroviral vectors that might be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells. They are also highly efficient at transducing human epithelial cells.

Lentiviral vectors for use in the methods herein may be derived from human and non-human (including SIV) lentiviruses. Examples of lentiviral vectors include nucleic acid sequences required for vector propagation as well as a tissue-specific promoter operably linked to a SDF-1 gene. These former may include the viral LTRs, a primer binding site, a polypurine tract, att sites, and an encapsidation site.

A lentiviral vector may be packaged into any suitable lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN) might also be used herein. Use of alphaviruses is described in Lundstrom, K., Intervirology 43:247-257, 2000 and Perri et al., Journal of Virology 74:9802-9807, 2000.

Recombinant, replication-defective alphavirus vectors are advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

In many of the viral vectors compatible with methods of the application, more than one promoter can be included in the vector to allow more than one heterologous gene to be expressed by the vector. Further, the vector can comprise a sequence which encodes a signal peptide or other moiety which facilitates the expression of a SDF-1 gene product from the target cell.

To combine advantageous properties of two viral vector systems, hybrid viral vectors may be used to deliver a SDF-1 nucleic acid to a target tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000. Retroviral genomes contained within an adenovirus may integrate within the target cell genome and effect stable SDF-1 gene expression.

Other nucleotide sequence elements which facilitate expression of the SDF-1 gene and cloning of the vector are further contemplated. For example, the presence of enhancers upstream of the promoter or terminators downstream of the coding region, for example, can facilitate expression.

In accordance with another aspect of the application, a tissue-specific promoter, can be fused to a SDF-1 gene. By fusing such tissue specific promoter within the adenoviral construct, transgene expression is limited to a particular tissue. The efficacy of gene expression and degree of specificity provided by tissue specific promoters can be determined, using the recombinant adenoviral system described herein.

In addition to viral vector-based methods, non-viral methods may also be used to introduce a SDF-1 nucleic acid into a target cell. A review of non-viral methods of gene delivery is provided in Nishikawa and Huang, Human Gene Ther. 12:861-870, 2001. An example of a non-viral gene delivery method according to the invention employs plasmid DNA to introduce a SDF-1 nucleic acid into a cell. Plasmid-based gene delivery methods are generally known in the art. In one example, the plasmid vector can have a structure as shown schematically in FIG. 7. The plasmid vector of FIG. 7 includes a CMV enhancer and CMV promoter upstream of an SDF-1α cDNA (RNA) sequence.

Optionally, a synthetic gene transfer molecules can be designed to form multimolecular aggregates with plasmid SDF-1 DNA. These aggregates can be designed to bind to cells of weakened region, ischemic region, and/or peri-infarct region of the myocardial tissue. Cationic amphiphiles, including lipopolyamines and cationic lipids, may be used to provide receptor-independent SDF-1 nucleic acid transfer into target cells (e.g., cardiomyocytes). In addition, preformed cationic liposomes or cationic lipids may be mixed with plasmid DNA to generate cell-transfecting complexes. Methods involving cationic lipid formulations are reviewed in Felgner et al., Ann. N.Y. Acad. Sci. 772:126-139, 1995 and Lasic and Templeton, Adv. Drug Delivery Rev. 20:221-266, 1996. For gene delivery, DNA may also be coupled to an amphipathic cationic peptide (Fominaya et al., J. Gene Med. 2:455-464, 2000).

Methods that involve both viral and non-viral based components may be used herein. For example, an Epstein Barr virus (EBV)-based plasmid for therapeutic gene delivery is described in Cui et al., Gene Therapy 8:1508-1513, 2001. Additionally, a method involving a DNA/ligand/polycationic adjunct coupled to an adenovirus is described in Curiel, D. T., Nat. Immun. 13:141-164, 1994.

Additionally, the SDF-1 nucleic acid can be introduced into the target cell by transfecting the target cells using electroporation techniques. Electroporation techniques are well known and can be used to facilitate transfection of cells using plasmid DNA.

Vectors that encode the expression of SDF-1 can be delivered to the target cell in the form of an injectable preparation containing pharmaceutically acceptable carrier, such as saline, as necessary. Other pharmaceutical carriers, formulations and dosages can also be used in accordance with the present invention.

Figure 7:
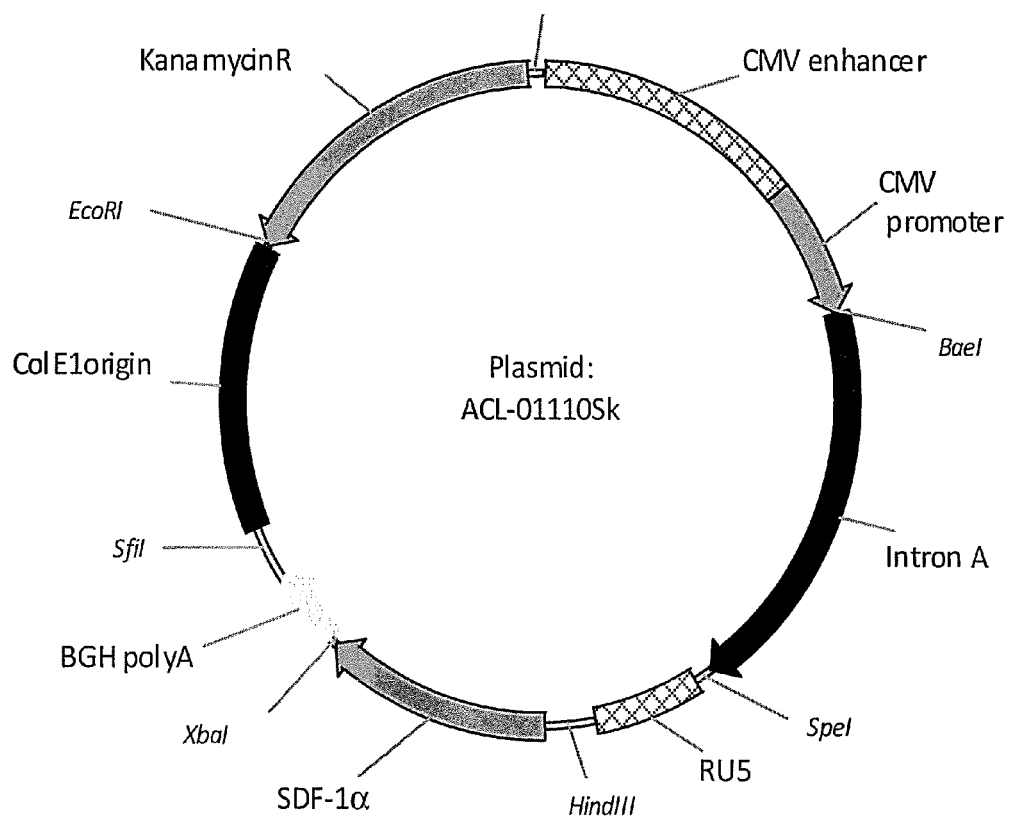
FIG. 7 is a schematic diagram of a plasmid vector in accordance with an aspect of the application.

In one aspect of the invention, the vector can comprise an SDF-1 plasmid, such as for example in FIG. 7. SDF-1 plasmid can be delivered to cells of the weakened region, ischemic region, and/or peri-infarct region of the myocardial tissue by direct injection of the SDF-1 plasmid vector into the weakened region, ischemic region, and/or peri-infarct region of the myocardial tissue at an amount effective to improve at least one myocardial functional parameters, such as left ventricular volume, left ventricular area, left ventricular dimension, or cardiac function as well as improve the subject's 6-minute walk test (6MWT) or New York Heart Association (NYHA) functional classification. By injecting the vector directly into or about the periphery of the weakened region, ischemic region, and/or peri-infarct region of the myocardial tissue, it is possible to target the vector transfection rather effectively, and to minimize loss of the recombinant vectors. This type of injection enables local transfection of a desired number of cells, especially about the weakened region, ischemic region, and/or peri-infarct region of the myocardial tissue, thereby maximizing therapeutic efficacy of gene transfer, and minimizing the possibility of an inflammatory response to viral proteins.

In an aspect of the application, the SDF-1 plasmid can be administered to the weakened, ischemic, and/or peri-infarct region in multiple injections of a solution of SDF-1 expressing plasmid DNA with each injection comprising about 0.33 mg/ml to about 5 mg/ml of SDF-1 plasmid/solution. In one example, the SDF-1 plasmid can be administered to the weakened, ischemic, and/or peri-infarct region in at least about 10 injections, at least about 15 injections, or at least about 20 injections. Multiple injections of the SDF-1 plasmid to the weakened, ischemic, and/or peri-infarct region allows a greater area and/or number of cells of the weakened, ischemic, and/or peri-infarct region to be treated.

Each injection administered to the weakened, ischemic, and/or peri-infarct region can have a volume of at least about 0.2 ml. The total volume of solution that includes the amount of SDF-1 plasmid administered to the weakened, ischemic, and/or peri-infarct region that can improve at least one functional parameter of the heart is at least about 10 ml.

In one example, the SDF-1 plasmid can be administered to the weakened, ischemic, and/or peri-infarct region in at least about 10 injections. Each injection administered to the weakened, ischemic, and/or peri-infarct region can have a volume of at least about 0.2 ml. The SDF-1 can be expressed in the weakened, ischemic, and/or peri-infarct region for greater than about three days.

For example, each injection of solution including SDF-1 expressing plasmid can have an injection volume of at least about 0.2 ml and an SDF-1 plasmid concentration per injection of about 0.33 mg/ml to about 5 mg/ml. In another aspect of the application, at least one functional parameter of the of the heart can be improved by injecting the SDF-1 plasmid into the weakened, ischemic, and/or peri-infarct region of the heart at an injection volume per site of at least about 0.2 ml, in at least about 10 injection sites, and at an SDF-1 plasmid concentration per injection of about 0.33 mg/ml to about 5 mg/ml.

It was found in a porcine model of congestive heart failure that injections of a solution of SDF-1 plasmid having concentration of less about 0.33 mg/ml or greater than about 5 mg/ml and an injection volume per injection site less than about 0.2 ml to a porcine model of heart failure resulted in little if any functional improvement of the left ventricular volume, left ventricular area, left ventricular dimension, or cardiac function of the treated heart.

In another aspect of the application, the amount of SDF-1 plasmid administered to the weakened, ischemic, and/or peri-infarct region that can improve at least one functional parameter of the heart is greater than about 4 mg and less than about 100 mg per therapeutic intervention. The amount of SDF-1 plasmid administered by therapeutic intervention herein refers to the total SDF-1 plasmid administered to the subject during a therapeutic procedure designed to affect or elicit a therapeutic effect. This can include the total SDF-1 plasmid administered in single injection for a particular therapeutic intervention or the total SDF-1 plasmid that is administered by multiple injections for a therapeutic intervention. It was found in a porcine model of congestive heart failure that administration of about 4 mg SDF-1 plasmid DNA via direct injection of the SDF-1 plasmid to the heart resulted in no functional improvement of the left ventricular volume, left ventricular area, left ventricular dimension, or cardiac function of the treated heart. Moreover, administration of about 100 mg of SDF-1 plasmid DNA via direct injection of the SDF-1 plasmid to the heart resulted in no functional improvement of the left ventricular volume, left ventricular area, left ventricular dimension, or cardiac function of the treated heart.

In some aspects of the application, the SDF-1 can be expressed at a therapeutically effective amount or dose in the weakened, ischemic, and/or peri-infarct region after transfection with the SDF-1 plasmid vector for greater than about three days. Expression of SDF-1 at a therapeutically effective dose or amount for greater three days can provide a therapeutic effect to weakened, ischemic, and/or peri-infarct region. Advantageously, the SDF-1 can be expressed in the weakened, ischemic, and/or peri-infarct region after transfection with the SDF-1 plasmid vector at a therapeutically effective amount for less than about 90 days to mitigate potentially chronic and/or cytotoxic effects that may inhibit the therapeutic efficacy of the administration of the SDF-1 to the subject.

It will be appreciated that the amount, volume, concentration, and/or dosage of SDF-1 plasmid that is administered to any one animal or human depends on many factors, including the subject's size, body surface area, age, the particular composition to be administered, sex, time and route of administration, general health, and other drugs being administered concurrently. Specific variations of the above noted amounts, volumes, concentrations, and/or dosages of SDF-1 plasmid can be readily be determined by one skilled in the art using the experimental methods described below.

In another aspect of the application, the SDF-1 plasmid can be administered by direct injection using catheterization, such as endo-ventricular catheterization or intra-myocardial catheterization. In one example, a deflectable guide catheter device can be advanced to a left ventricle retrograde across the aortic valve. Once the device is positioned in the left ventricle, SDF-1 plasmid can be injected into the peri-infarct region (both septal and lateral aspect) area of the left ventricle. Typically, 1.0 ml of SDF-1 plasmid solution can be injection over a period of time of about 60 seconds. The subject be treated can receive at least about 10 injection (e.g., about 15 to about 20 injections in total).

The myocardial tissue of the subject can be imaged prior to administration of the SDF-1 plasmid to define the area of weakened, ischemic, and/or peri-infarct region prior to administration of the SDF-1 plasmid. Defining the weakened, ischemic, and/or peri-infarct region by imaging allows for more accurate intervention and targeting of the SDF-1 plasmid to the weakened, ischemic, and/or peri-infarct region. The imaging technique used to define the weakened, ischemic, and/or peri-infarct region of the myocardial tissue can include any known cardio-imaging technique. Such imaging techniques can include, for example, at least one of echocardiography, magnetic resonance imaging, coronary angiogram, electroanatomical mapping, or fluoroscopy. It will be appreciated that other imaging techniques that can define the weakened, ischemic, and/or peri-infarct region can also be used.

Optionally, other agents besides SDF-1 nucleic acids (e.g., SDF-1 plasmids) can be introduced into the weakened, ischemic, and/or peri-infarct region of the myocardial tissue to promote expression of SDF-1 from cells of the weakened, ischemic, and/or peri-infarct region. For example, agents that increase the transcription of a gene encoding SDF-1 increase the translation of an mRNA encoding SDF-1, and/or those that decrease the degradation of an mRNA encoding SDF-1 could be used to increase SDF-1 protein levels. Increasing the rate of transcription from a gene within a cell can be accomplished by introducing an exogenous promoter upstream of the gene encoding SDF-1. Enhancer elements, which facilitate expression of a heterologous gene, may also be employed.

Other agents can include other proteins, chemokines, and cytokines, that when administered to the target cells can upregulate expression SDF-1 form the weakened, ischemic, and/or peri-infarct region of the myocardial tissue. Such agents can include, for example: insulin-like growth factor (IGF)-1, which was shown to upregulate expression of SDF-1 when administered to mesenchymal stem cells (MSCs) (Circ. Res. 2008, Nov. 21; 103(11):1300-98); sonic hedgehog (Shh), which was shown to upregulate expression of SDF-1 when administered to adult fibroblasts (Nature Medicine, Volume 11, Number 11, November 23); transforming growth factor β (TGF-β); which was shown to upregulate expression of SDF-1 when administered to human peritoneal mesothelial cells (HPMCs); IL-1β, PDGF, VEGF, TNF-α, and PTH, which are shown to upregulate expression of SDF-1, when administered to primary human osteoblasts (HOBs) mixed marrow stromal cells (BMSCs), and human osteoblast-like cell lines (Bone, 2006, April; 38(4): 497-508); thymosin β4, which was shown to upregulate expression when administered to bone marrow cells (BMCs) (Curr. Pharm. Des. 2007; 13(31):3245-51; and hypoxia inducible factor 1α (HIF-1), which was shown to upregulate expression of SDF-1 when administered to bone marrow derived progenitor cells (Cardiovasc. Res. 2008, E. Pub.). These agents can be used to treat specific cardiomyopathies where such cells capable of upregulating expression of SDF-1 with respect to the specific cytokine are present or administered.

The SDF-1 protein or agent, which causes increases, and/or upregulates expression of SDF-1, can be administered to the weakened, ischemic, and/or peri-infarct region of the myocardial tissue neat or in a pharmaceutical composition. The pharmaceutical composition can provide localized release of the SDF-1 or agent to the cells of the weakened, ischemic, and/or peri-infarct region being treated. Pharmaceutical compositions in accordance with the application will generally include an amount of SDF-1 or agent admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. Moreover, for human administration, preparations should meet sterility, pyrogenicity, general safety and purity standards as required by FDA Office of Biological Standards.

The pharmaceutical composition can be in a unit dosage injectable form (e.g., solution, suspension, and/or emulsion). Examples of pharmaceutical formulations that can be used for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol, and the like), dextrose, saline, or phosphate-buffered saline, suitable mixtures thereof and vegetable oils.

Proper fluidity can be maintained, for example, by the use of a coating, such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions.

Additionally, various additives, which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to methods described herein, however, any vehicle, diluent, or additive used would have to be compatible with the compounds.

Sterile injectable solutions can be prepared by incorporating the compounds utilized in practicing the methods described herein in the required amount of the appropriate solvent with various amounts of the other ingredients, as desired.

Pharmaceutical "slow release" capsules or "sustained release" compositions or preparations may be used and are generally applicable. Slow release formulations are generally designed to give a constant drug level over an extended period and may be used to deliver the SDF-1 or agent. The slow release formulations are typically implanted in the vicinity of the weakened, ischemic, and/or peri-infarct region of the myocardial tissue.

Examples of sustained-release preparations include semi-permeable matrices of solid hydrophobic polymers containing the SDF-1 or agent, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and $\gamma$ ethyl-L-glutamate; non-degradable ethylene-vinyl acetate; degradable lactic acid-glycolic acid copolymers, such as the LUPRON DEPOT (injectable microspheres composed of lactic acid-glycolic acid copolymer and leuprolide acetate); and poly-D-(−)-3-hydroxybutyric acid.

While polymers, such as ethylene-vinyl acetate and lactic acid-glycolic acid enable release of molecules for over 100 days, certain hydrogels release proteins for shorter time periods. When encapsulated, SDF-1 or the agent can remain in the body for a long time, and may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thio-disulfide interchange, stabilization is achieved by modifying sulfhydryl residues, lyophilizing from acidic solutions, controlling moisture content, using appropriate additives, developing specific polymer matrix compositions, and the like.

In certain embodiments, liposomes and/or nanoparticles may also be employed with the SDF-1 or agent. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the methods, and such particles may be are easily made.

For preparing pharmaceutical compositions from the compounds of the application, pharmaceutically acceptable carriers can be in any form (e.g., solids, liquids, gels, etc.). A solid carrier can be one or more substances, which may also act as diluents, flavoring agents, binders, preservatives, and/or an encapsulating material. The following examples are for the purpose of illustration only and are not intended to limit the scope of the claims, which are appended hereto.

EXAMPLES

Example 1

Stromal cell-derived factor-1 or SDF-1 is a naturally-occurring chemokine whose expression is rapidly upregulated in response to tissue injury. SDF-1 induction stimulates a number of protective anti-inflammatory pathways, causes the down regulation of pro-inflammatory mediators (such as MMP-9 and IL-8), and can protect cells from apoptosis. Furthermore, SDF-1 is a strong chemoattractant of organ specific and bone marrow derived stem cells and progenitor cells to the site of tissue damage, which promotes tissue preservation and blood vessel development. Based on observations that increased expression of SDF-1 led to improved cardiac function in ischemic animal models, we focused on developing a non-viral, naked-DNA SDF-1-encoding plasmid for treatment of ischemic cardiovascular disease. During the course of development, the plasmid was optimized based on cell culture and small animal study results described below. The plasmid ACL-01110Sk was selected based on its ability to express transgenes in cardiac tissue and to consistently improve cardiac function in pre-clinical animal models of ischemic cardiomyopathy. SDF-1 transgene expression in ACL-01110Sk is driven by the CMV enhancer/promoter, CMV-intron A, and the RU5 translational enhancer. The drug product, JVS-100 (formerly ACRX-100), is composed of plasmid ACL-01110Sk in 5% dextrose.

Initial studies in a rat model of heart failure demonstrated that ACL-01110S (an SDF-1 expressing precursor to ACL-01110Sk) improved cardiac function after injection of the plasmid directly into the infarct border zone of the rat hearts four weeks following an MI. Benefits were sustained for at least 8-10 weeks post-injection and correlated with increased vasculogenesis in the ACL-01110S treated animals. ACL-01110S was modified to optimize its expression profile. The plasmid ACL-01110Sk was deposited with the Amer. Type Cult. Coll. (10801 University Blvd., Manassas, Va. 20110-2209) on Nov. 14, 2012 and has been assigned Accession No. PTA-13320.

Plasmid Dose-Dependent Expression in a Rat Model of MI

To determine the plasmid dose per injection that would provide maximal expression in rat cardiac tissue, escalating doses (10, 50, 100, 500 µg) of the ACL-00011L luciferase plasmid were injected into infarcted rat hearts. Lewis rats were subjected to a median sternotomy and the left anterior descending artery (LAD) was permanently ligated, and injected peri-MI at one site with 100 µl ACL-00011L plasmid in PBS. Whole body luciferase expression was measured in each dose cohort (n=3) by non-invasive bioluminescent imaging (Xenogen, Hopkinton, Mass.) at baseline and at 1, 2, 3, 4, and 5 days post-injection. The peak expression increased up to a dose of 100 µg and saturated at higher doses. Based on this dose-response curve, a dose of 100 µg was determined to be sufficient for maximal plasmid expression in rat hearts. ACL-00011L expressed the luciferase gene from a vector backbone equivalent to that used in construction of ACL-00011S, which expresses SDF-1.

Comparison of Cardiac Vector Expression in a Rat Model of Ischemic Heart Failure The luciferase expressing equivalents of several SDF-1 plasmid candidates were tested for expression in cardiac tissue in a rat model of myocardial infarct (MI). Plasmid candidates differed in the promoters driving expression and presence of enhancer elements. Lewis rats were subjected to a median sternotomy and the left anterior descending artery (LAD) was permanently ligated and the chest was closed. Four weeks later, the chest was reopened, and the luciferase expressing plasmids was directly injected (100 µg in 100 µl per injection) into 4 peri-Myocardial infarction sites. At 1, 2, 4, 6, 8, and 10 days post-injection (and every 3-4 days following), rats were anesthetized, injected with luciferin and imaged with a whole-body Xenogen Luciferase imaging system.

The two CMV driven plasmids tested, ACL-00011L and ACL-01110L yielded detectable luciferase expression within 24 hours of injection with an initial peak of expression at 2 days post-injection.

ACL-01110L peak expression was 7 times greater than ACL-00011L and expression was approximately 10 days longer (lasting up to 16 days post injection). In contrast, ACL-00021L (αMHC driven plasmid) showed no initial peak, but expressed at a low-level through day 25 post-injection. These results support previous studies demonstrating that CMV driven plasmids can be used for localized, transient protein expression in the heart and that the timeframe of therapeutic protein expression can be modulated through the inclusion of enhancer elements.

Efficacy of SDF-1 Plasmids in Rat Model of MI

SDF-1-encoding plasmids were tested in a rat model of MI to determine if functional cardiac benefit could be achieved. Lewis rats were subjected to a median sternotomy and the LAD was permanently ligated immediately distal to the first bifurcation. Four weeks later, the chest was reopened, and one of three SDF-1 expressing plasmids (ACL-01110S, ACL-00011S, or ACL-00021S) or saline was injected (100 µg per 100 µl injection) into 4 peri-MI sites:

At baseline (pre-injection), and 2, 4, and 8 weeks post-injection, rats were anesthetized and imaged with M-mode echocardiography. LVEF, fractional shortening, and LV dimensions were measured by a trained sonographer who was blinded to randomization.

A strong trend in improvement in cardiac function was observed with both CMV driven plasmids, ACL-01110S and ACL-00011S, compared to saline controls. ACL-01110S elicited a statistically significant increase in fractional shortening at four weeks that was sustained 8 weeks after injection. In contrast, no difference in function was observed between αMHC driven plasmid ACL-00021S and saline. Furthermore, compared to control, the ACL-01110S and the ACL-00011S-treated animals had significant increases in large vessel density (ACL-01110S: 21±1.8 vessels/mm$^2$; ACL-00011S: 17±1.5 vessels/mm$^2$; saline: 6±0.7 vessels/mm$^2$, p<0.001 for both vs. saline) and reduced infarct size (ACL-01110S: 16.9±2.8%; ACL-00011S: 17.8±2.6%; saline: 23.8±4.5%). Importantly, treatment with ACL-01110S demonstrated the largest improvement in cardiac function and vasculogenesis, and caused the largest reduction in infarct size.

In summary, in a rat model of ischemic heart failure, both SDF-1-encoding plasmids driven by a CMV promoter provided functional cardiac benefit, increased vasculogenesis, and reduction in infarct size compared to saline treatment. In all parameters tested, ACL-01110S provided the most significant benefit.

Transfection Efficiency of ACL-01110Sk and ACl-01010Sk in H9C2 Cells

In vitro transfection of H9C2 myocardial cells without transfection reagents (i.e.,—naked plasmid DNA was added to cells in culture) were used to estimate in vivo transfection efficiencies of GFP versions of Juventas lead plasmid vectors, ACL-01110Sk and ACL-01010Sk. H9C2 cells were cultured in vitro and various amounts of pDNA (0.5 µg, 2.0 µg, 4.0 µg, 5.0 µg) were added in 5% dextrose. The GFP vectors were constructed from the ACL-01110Sk (ACL-01110G) or ACL-01010Sk (ACL-01010G) backbones. At Day 3 post-transfection, GFP fluorescence was assessed by FACS to estimate transfection efficiency. The transfection efficiencies for the ACL-01110G and ACL-01010G vectors in 5% dextrose ranged from 1.08-3.01%. At each amount of pDNA tested, both vectors had similar in vitro transfection efficiencies. We conclude that the 1-3% transfection efficiency observed in this study is in line with findings from previous studies demonstrating a similar level of in vivo transfection efficiency. Specifically, JVS-100 will transfect a limited but sufficient number of cardiac cells to produce therapeutic amounts of SDF-1.

Example 2

Expression of Plasmid in Porcine Myocardium

A porcine occlusion/reperfusion MI model of the left anterior descending artery (LAD) was selected as an appropriate large animal model to test the efficacy and safety of ACRX-100. In this model, 4 weeks recovery is given between MI and treatment to allow time for additional cardiac remodeling and to simulate chronic ischemic heart failure.

Surgical Procedure

Yorkshire pigs were anesthesitzed and heparanized to an activated clotting time (ACT) of ≧300 seconds, and positioned in dorsal recumbency. To determine the contour of the LV, left ventriculography was performed in both the Anterior—Posterior and Lateral views.

Delivery of Luciferase Plasmid into Porcine Myocardium

A deflectable guide catheter device was advanced to the left ventricle retrograde across the aortic valve, the guide wire was removed, and an LV endocardial needle injection catheter was entered through the guide catheter into the LV cavity.

Luciferase plasmid was injected at 4 sites at a given volume and concentration were made into either the septal or lateral wall of the heart. Five combinations of plasmid concentration (0.5, 2, or 4 mg/ml) and site injection volumes (0.2, 0.5, 1.0 ml) were tested. Plasmid at 0.5 mg/ml was buffered in USP Dextrose, all others were buffered in USP Phosphate Buffered Saline. For each injection, the needle was inserted into the endocardium, and the gene solution was injected at a rate of 0.8-1.5 ml/minute. Following injection, the needle was held in place for 15 seconds and then withdrawn. After injections were completed, all instrumentation was removed, the incision was closed, and the animal was allowed to recover.

Harvesting of Myocardial Tissue

On Day 3 post injection, the animals were submitted to necropsy. Following euthanasia, the heart was removed, weighed, and perfused with Lactate Ringers Solution until clear of blood. The LV was opened and the injection sites identified. A 1 cm square cube of tissue was taken around each injection site. Four (4) cubes harvested from the posterior wall remote from any injection sites served as negative controls. The tissue samples were frozen in liquid nitrogen and stored at −20 to −70° C.

Assessment of Luciferase Expression

The tissue samples were thawed and placed in a 5 ml glass tube. Lysis buffer (0.5-1.0 ml) was added and tissue was disrupted using Polytron homogenization (model PT1200) on ice. Tissue homogenate was centrifuged and protein concentration of the supernatant was determined for each tissue sample using the Bio-rad Detergent-Compatible (DC) protein assay and a standard curve of known amounts of bovine serum albumin (BSA). Tissue sample homogenate (1-10 μl) was assayed using the Luciferase assay kit (Promega).

The results of the experiment are shown in FIG. 1. The data shows that expression of the vector increases with increasing injection volume and increasing concentration of DNA.

Example 3

Improvement in Cardiac Function by SDF-1 Plasmid Treatment in Porcine Model of Ischemic Cardiomyopathy Induction of Myocardial Infarction Yorkshire pigs were anesthesitzed and heparanized to an activated clotting time (ACT) of ≧250 seconds, and positioned in dorsal recumbency. A balloon catheter was introduced by advancing it through a guide catheter to the LAD to below the first major bifurcation of the LAD. The balloon was then inflated to a pressure sufficient to ensure complete occlusion of the artery, and left inflated in the artery for 90-120 minutes. Complete balloon inflation and deflation was verified with fluoroscopy. The balloon was then removed, the incision was closed, and the animal was allowed to recover.

Enrollment Criteria

One month post-MI, cardiac function in each pig was assessed by echocardiography. If the LVEF was less than 40% and the LVESV was greater than 56.7 ml, the pig was enrolled in the study.

Surgical Procedure

Each enrolled pig was anesthesitzed and heparanized to an activated clotting time (ACT) of ≧300 seconds, and positioned in dorsal recumbency. To determine the contour of the LV, left ventriculography was performed in both the Anterior—Posterior and Lateral views.

Delivery of SDF-1 Plasmid (ACL-01110Sk) into Myocardium

Each pig was randomized to one of 3 sacrifice points: 3 days, 30 days, or 90 days post-treatment, and to one of four treatment groups: control (20 injections, buffer only), low (15 injections, 0.5 mg/ml), mid (15 injections, 2.0 mg/ml), or high (20 injections, 5.0 mg/ml). All plasmid was buffered in USP Dextrose. The injection procedure is described below.

A deflectable guide catheter device was advanced to the left ventricle retrograde across the aortic valve, the guide wire was removed, and an LV endocardial needle injection catheter was entered through the guide catheter into the LV cavity. SDF-1 plasmid or buffer at randomized dose was loaded into 1 ml syringes that were connected to the catheter. Each injection volume was 1.0 ml. For each injection, the needle was inserted into the endocardium, and the solution was injected over 60 seconds. Following injection, the needle was held in place for 15 seconds and then withdrawn. After injections were completed, all instrumentation was removed, the incision was closed, and the animal was allowed to recover.

At sacrifice, samples of tissues from the heart and other major organs were excised and flash frozen for PCR and histopathological analysis.

Assessment of Cardiac Function

Each animal had cardiac function assessed by standard 2-dimensional echocardiography at day 0, 30, 60, and 90 post-injection (or until sacrifice). Measurements of left ventricular volume, area, and wall motion score were made by an independent core laboratory. The efficacy parameters measured are shown below in Table 1.

TABLE 1

Echocardiographic Parameters

| Variable Name | Definition |
|---|---|
| LVESV | End Systolic Volume measured in parasternal long-axis view |
| LVEDV | End Diastolic Volume measured in parasternal long-axis view |
| LVEF | (LVEDV − LVESV)/LVEDV * 100% |
| WMSI | Average of all readable wall motion scores based on ASE 17 segment model and scoring system of 0-5. |

Figure 2:
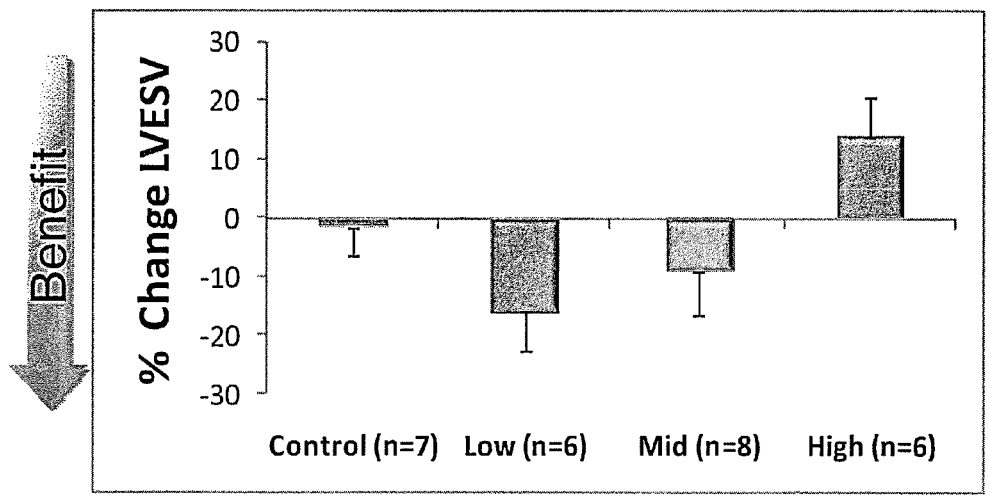
FIG. 2 is a chart illustrating % change of left ventricular end systolic volume for various amounts of SDF-1 plasmid using a porcine model of congestive heart failure 30 days following SDF-1 injection.
Figure 3:
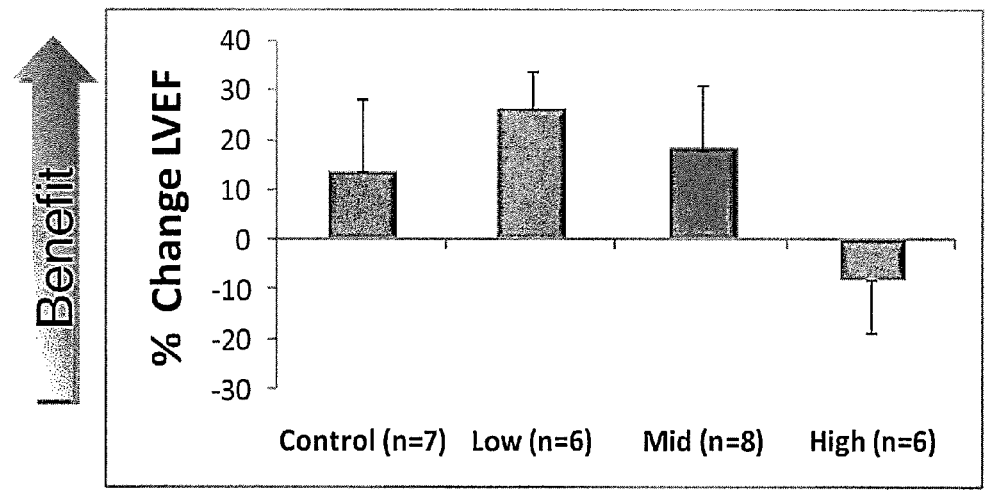
FIG. 3 is a chart illustrating % change of left ventricular ejection fraction for various amounts of SDF-1 plasmid using a porcine model of congestive heart failure 30 days following SDF-1 injection.
Figure 4:
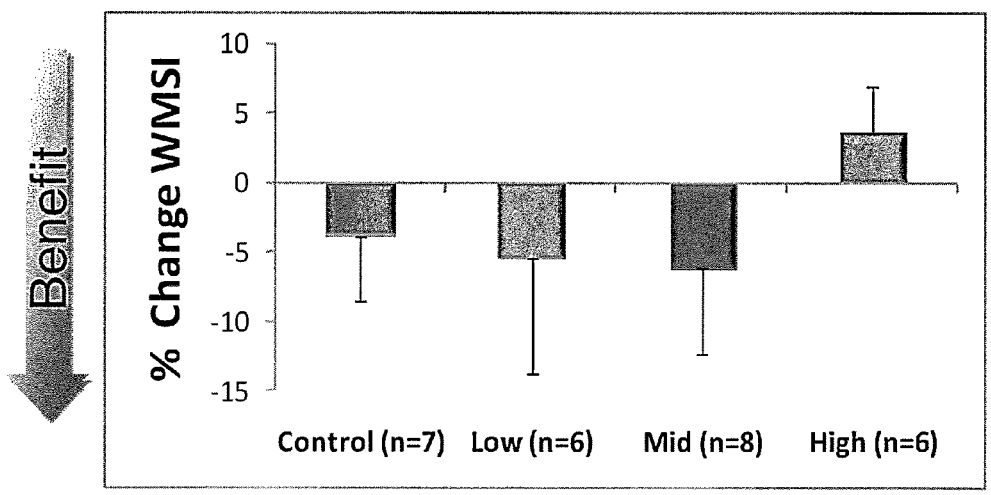
FIG. 4 is a chart illustrating % change in wall motion score index for various amounts of SDF-1 plasmid using a porcine model of congestive heart failure 30 days following SDF-1 injection.
Figure 5:
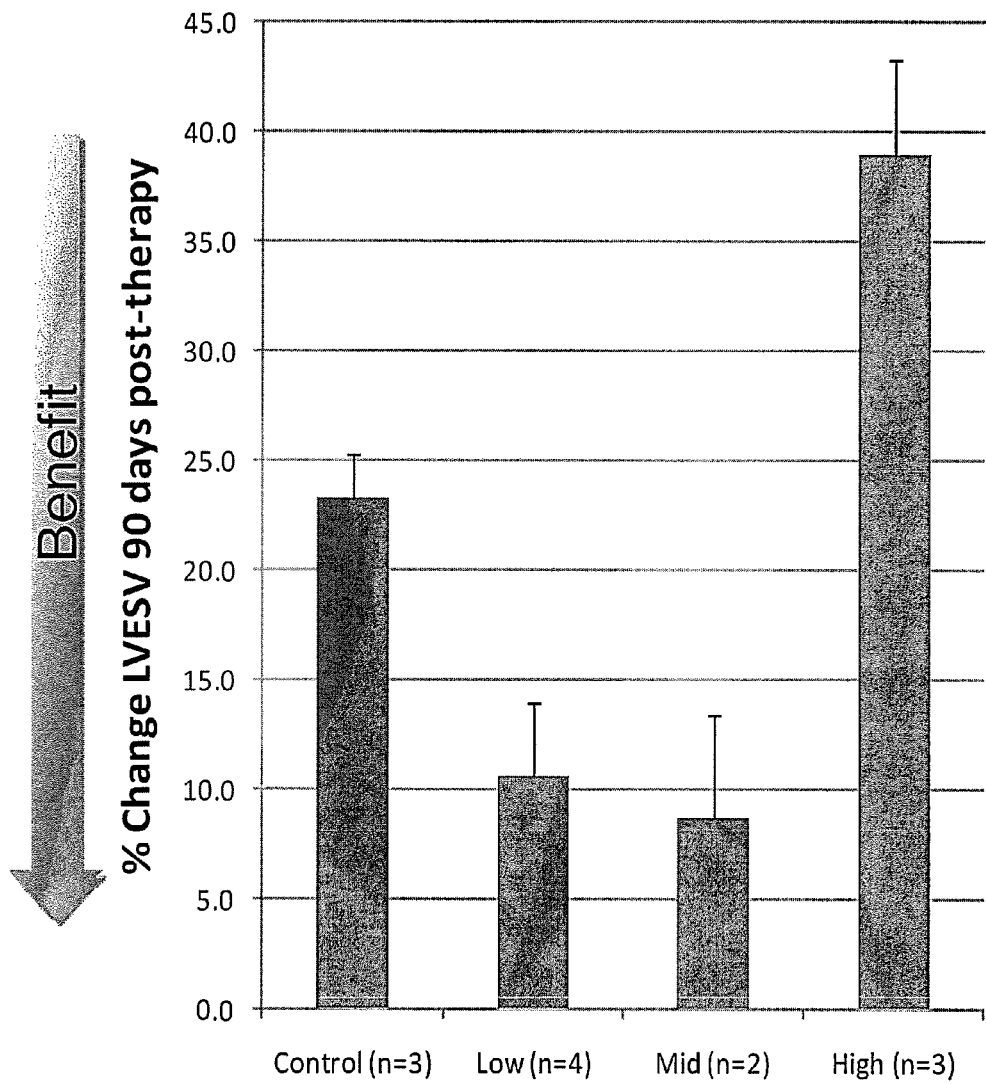
FIG. 5 is a chart illustrating % change of left ventricular end systolic volume for various amounts of SDF-1 plasmid using a porcine model of congestive heart failure 90 days following SDF-1 injection.

The impact of SDF-1 plasmid on functional improvement is shown in FIGS. 2-5. FIGS. 2-4 show that the low and mid doses of SDF-1 plasmid improve LVESV, LVEF, and Wall Motion Score Index at 30 days post-injection compared to control; whereas, the high dose does not show benefit. FIG. 5 demonstrates that the cardiac benefit in the low and mid dose is sustained to 90 days, as both show a marked attenuation in pathological remodeling, that is, a smaller increase in LVESV, compared to control.

Assessment of Vasculogenesis

Animals that were sacrificed at 30 days were assessed for vessel density in the left ventricle using 7 to 9 tissue samples harvested from each formalin-fixed heart. Genomic DNA was extracted and efficiently purified from formalin fixed tissue sample using a mini-column purification procedure (Qiagen). Samples from SDF-1 treated and control animals were tested for presence of plasmid DNA by quantitative PCR. Three to five tissue samples found to contain copies of plasmid DNA at least 4-fold above background (except in control animals) for each animal were used to prepare slides and immunostained with isolectin. Cross-sections were identified and vessels counted in 20-40 random fields per tissue. The vessels per field were converted to vessels/mm$^2$ and were averaged for each animal. For each dose, data is reported as the average vessels/mm$^2$ from all animals receiving that dose.

Figure 6:
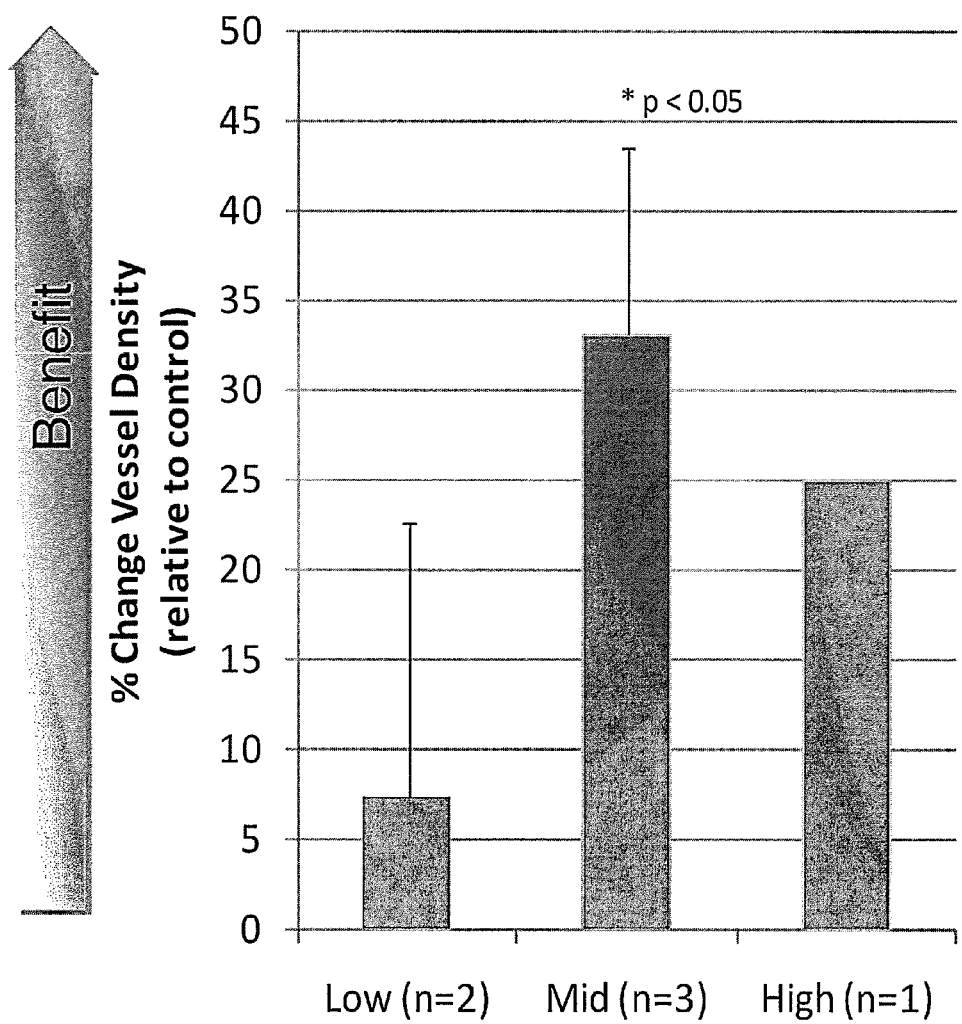
FIG. 6 is a chart illustrating % change of vessel density for various amounts of SDF-1 plasmid using a porcine model of congestive heart failure 30 days following SDF-1 injection.

FIG. 6 shows that both doses that provided functional benefit also significantly increase vessel density at 30 days compared to control. In contrast, the high dose, which did not improve function, did not substantially increase vessel density. This data provides a putative biologic mechanism by which SDF-1 plasmid is improving cardiac function in ischemic cardiomyopathy.

Biodistribution Data

JVS-100 distribution in cardiac and non-cardiac tissues was measured 3, 30 and 90 days after injection in the pivotal efficacy and toxicology study in the pig model of MI. In cardiac tissue, at each time point, average JVS-100 plasmid concentration increased with dose. Art each dose, JVS-100 clearance was observed at 3, 30 and 90 days following injection with approximately 99.999999% cleared from cardiac tissue at Day 90. JVS-100 was distributed to non-cardiac organs with relatively high blood flow (e.g. heart, kidney, liver, and lung) with the highest concentrations noted 3 days following injection. JVS-100 was present primarily in the kidney, consistent with renal clearance of the plasmid. There were low levels of persistence at 30 days and JVS-100 was essentially undetectable in non-cardiac tissues at 90 days.

Conclusions

Treatment with JVS-100 resulted in significantly increased blood vessel formation and improved heart function in pigs with ischemic heart failure following a single endomyocardial injection of 7.5 and 30 mg. The highest dose of JVS-100 tested (100 mg) showed a trend in increased blood vessel formation but did not show improved heart function. None of the doses of JVS-100 were associated with signs of toxicity, adverse effects on clinical pathology parameters or histopathology. JVS-100 was distributed primarily to the heart with approximately 99.999999% cleared from cardiac tissue at 90 days following treatment. JVS-100 was distributed to non-cardiac organs with relatively high blood flow (e.g., heart, kidney, liver, and lung) with the highest concentrations in the kidneys 3 days following injection. JVS-100 was essentially undetectable in the body 90 days after injection with only negligible amounts of the administered dose found in non-cardiac tissues. Based on these findings the no observed adverse effect level (NOAEL) for JVS-100 in the pig model of MI was 100 mg administered by endomyocardial injection.

Example 4

Porcine Exploratory Study: LUC Injections by Transarterial Injection in Chronic MI Pigs Methods One pig with a previous LAD occlusion/reperfusion MI and an EF>40%, was injected with ACL-01110Sk with a Transarterial catheter. Two injections in the LAD and 2 in the LCX were performed with an injection volume of 2.5 ml and a total injection time of 125-130 sec. One additional injection in the LCX of 3.0 ml with a total injection time of 150 sec was performed with conttast mixed with the plasmid.

Sacrifice and Tissue Collection

Three days following the injections, the animal was euthanized. After euthanasia, the heart was removed, drained of blood, placed on an ice cold cutting board and further dissected by the necropsy technician or pathologist. The non-injected myocardium from the septum was obtained via opening the right ventricle. The right ventricle was trimmed from the heart and placed in cold cardioplegia. New scalpel blades were used for each of the sections.

Next, the left ventricle was opened and the entire left ventricle was excised by slicing into 6 sections cutting from apex to base. The LV was evenly divided into 3 slices. Following excision, each section was able to lay flat. Each section (3 LV sections, 1 RV section, and 1 pectoral muscle) was placed in separate labeled containers with cold cardioplegia on wet ice, and transported for luciferase analysis.

Luciferase Imaging

All collected tissues were immersed in luciferin and imaged with a Xenogen imaging system to determine plasmid expression.

Results

Figure 8:
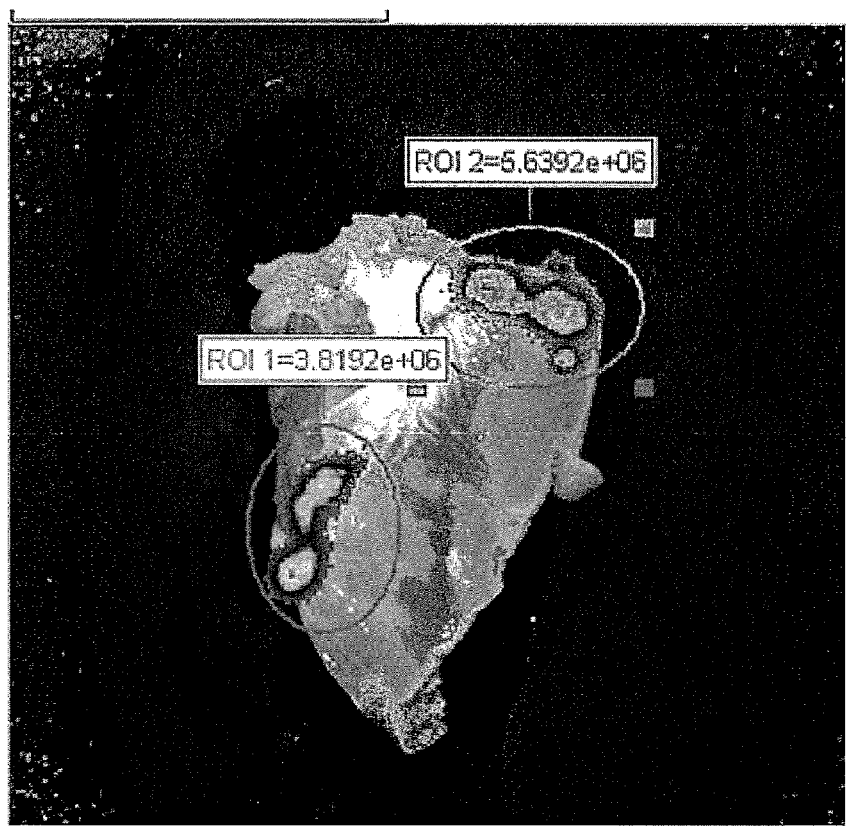
FIG. 8 is an image showing plasmid expression over a substantial portion of a porcine heart.
Figure 9:
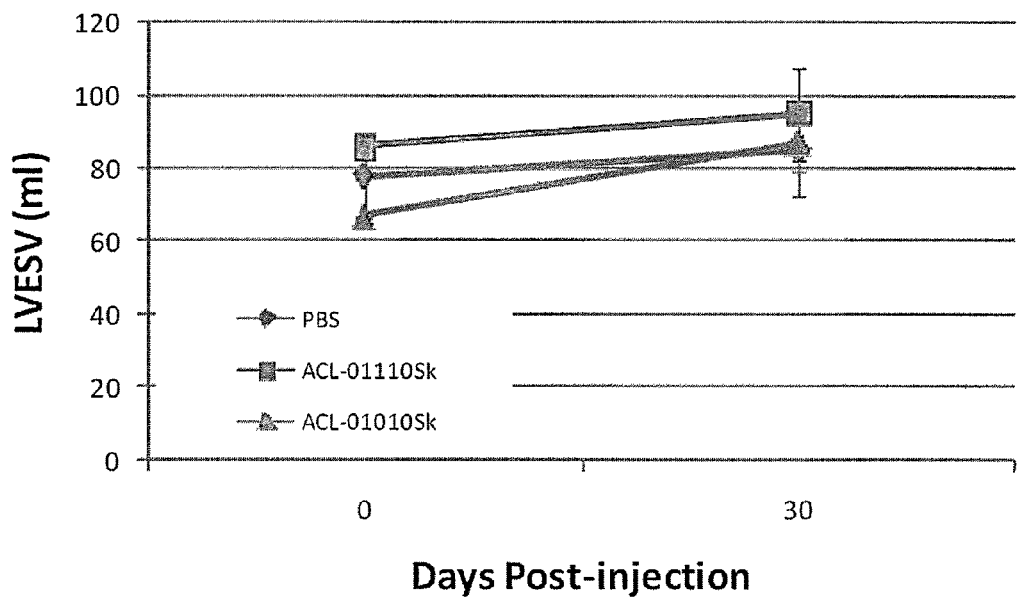
FIG. 9 is a chart illustrating left ventricular end systolic volume at baseline and 30 days post-initial injection. All groups show similar increases in left ventricular end systolic volume at 30 days. N=3 for all data points. Data presented as mean±SEM.
Figure 10:
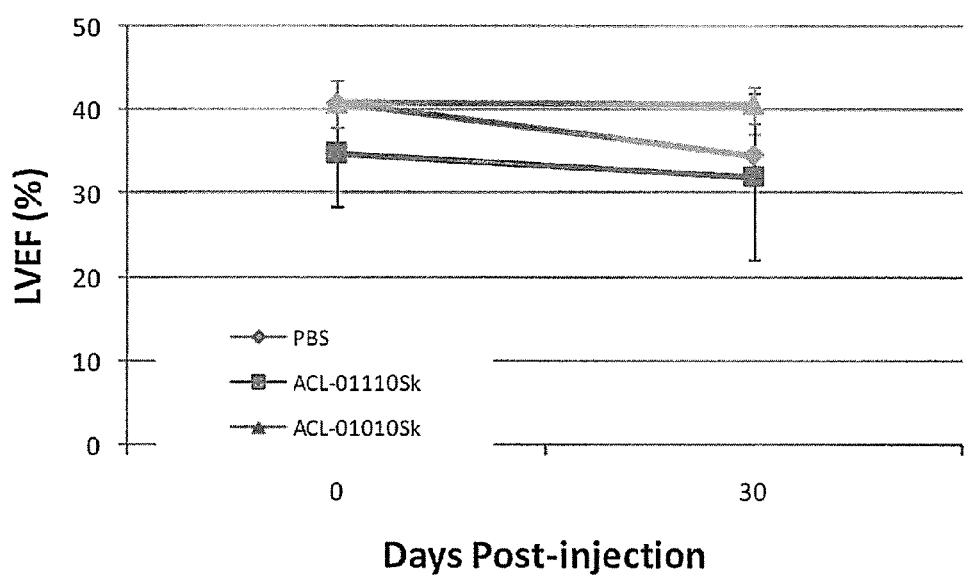
FIG. 10 is a chart illustrating left ventricular ejection fraction at baseline and 30 days post-initial injection. All groups show lack of improvement in left ventricular ejection fraction. N=3 for all data points. Data presented as mean±SEM.

A representative image of the heart is shown in FIG. 8. The colored spots denote areas of luciferase expression. These spots showed Relative Light Units (RLUs) of greater than $10^6$ units, more than 2 orders of magnitude above background. This data demonstrated that the catheter delivered plasmid sufficient to generate substantial plasmid expression over a significant portion of the heart.

Example 5

Clinical Study Example

Ascending doses of JVS-100 are administered to treat HF in subjects with ischemic cardiomyopathy. Safety is tracked at each dose by documenting all adverse events (AEs), with the primary safety endpoint being the number of major cardiac AEs at 30 days. In each cohort, subjects will receive a single dose of JVS-100. In all cohorts, therapy efficacy is evaluated by measuring the impact on cardiac function via standard echocardiography measurements, cardiac perfusion via Single Photon Emission Computed Tomography (SPECT) imaging, New York Heart Association (NYHA) class, six minute walk distance, and quality of life.

All subjects have a known history of systolic dysfunction, prior MI, and no current cancer verified by up to date age appropriate cancer screening. All subjects are screened with a physician visit, and a cardiac echocardiogram. Further baseline testing such as SPECT perfusion imaging, is performed. Each subject receives fifteen (15) 1 ml injections of JVS-100 delivered by an endocardial needle catheter to sites within the infarct border zone. Three cohorts (A, B, C) will be studied. As shown in Table 2, dose will be escalated by increasing the amount of DNA per injection site while holding number of injection sites constant at 15 and injection volume at 1 ml. Subjects are monitored for approximately 18 hours post-injection and have scheduled visits at 3 and 7 days post-injection to ensure that there are no safety concerns. The patient remains in the hospital for 18 hours after the injection to ensure all required blood collections (i.e., cardiac enzymes, plasma SDF-1 protein levels) are performed. All subjects have follow-up at 30 days (1 month), 120 days (4 months), and 360 days (12 months) to assess safety and cardiac function. The primary safety endpoint are major adverse cardiac events (MACE) within 1 month post-therapy delivery. AEs will be tracked for each subject throughout the study. The following safety and efficacy endpoints will be measured:

Safety:
    Number of Major Adverse Cardiac Events (MACE) at 30 days post-injection
    Adverse Events throughout the 12 month follow-up period
    Blood lab Analysis (Cardiac Enzymes, CBC, ANA)
    SDF-1 Plasma Levels
    Physical assessment
    Echocardiography
    AICD monitoring
    ECG Efficacy:

Change from baseline in LVESV, LVEDV, LVEF, and wall motion score index

Change from baseline in NYHA classification and quality of life

Change from baseline in perfusion as determined by SPECT imaging

Change from baseline in Six Minute Walk Test distance

TABLE 2

Clinical Dosing Schedule

| Cohort | # of Subjects | Amount of DNA/site | Injection volume/site | # Injection Sites | Total Dose of DNA |
|---|---|---|---|---|---|
| Cohort A | 4 | 0.33 mg | 1.0 ml | 15 | 5 mg |
| Cohort B | 6 | 1.0 mg | 1.0 ml | 15 | 15 mg |
| Cohort C | 6 | 2.0 mg | 1.0 ml | 15 | 30 mg |

Based on preclinical data, delivery of JVS-100 is expected to elicit an improvement cardiac function and symptoms at 4 months that sustains to 12 months. At 4 months following JVS-100 injection, compared to baseline values, an improvement in six minute walk distance of about greater than 30 meters, an improvement in quality of life score of about 10%, and/or an improvement of approximately 1 NYHA class are anticipated. Similarly, we expect a relative improvement in LVESV, LVEF, and/or WMSI of approximately 10% compared to baseline values.

Comparative Example 1

Evaluation of Cardiac Function by Echocardiography in Chronic Heart Failure Pigs after Treatment with ACL-01110Sk or ACL-01010Sk Purpose The purpose of this study is to compare functional cardiac response to SDF-1 plasmids ACL-01110Sk or ACL-01010Sk after endomyocardial catheter delivery in a porcine model of ischemic heart failure This study compared efficacy of ACL-01110Sk and ACL-01010Sk in improving function in a porcine ischemic heart failure model. In this study, the plasmids were delivered by an endoventricular needle injection catheter. Efficacy was assessed by measuring the impact of the therapy on cardiac remodeling (i.e., left ventricular volumes) and function (i.e., left ventricular ejection fraction (LVEF)) via echocardiography.

Methods

Briefly, male Yorkshire pigs were given myocardial infarctions by LAD occlusion via balloon angioplasty for 90 minutes. Pigs having an ejection fraction <40% as measured by M-mode echocardiography 30 days post-infarct were enrolled. Pigs were randomized to one of 3 groups to be injected with either Phosphate Buffered Saline (PBS, control), ACL-01110Sk in PBS, or ACL-01010Sk in PBS using an endoventricular needle injection catheter delivery system (Table 3).

TABLE 3

Initial Study Design: SDF-1 Therapy for Chronic Heart Failure in Pigs

| Group | Plasmid | # of Pigs | Injection volume/site | Amount of DNA/site | # Injection Sites | Total DNA |
|---|---|---|---|---|---|---|
| 1 | Vehicle | 3 | 200 µl | N/A | 10 | n/a |
| 2 | ACL-01010Sk | 3 | 200 µl | 400 µg | 10 | 4 mg |
| 3 | ACL-01110Sk | 3 | 200 µl | 400 µg | 10 | 4 mg |

Echocardiograms were recorded prior to injection and at 30 and 60 days post-injection. Table 8 below defines the variables as they are referred to in this report.

TABLE 4

Definition of variables

| Variable Name | Definition |
|---|---|
| LVESV | End Systolic Volume measured in parasternal long-axis view |
| LVEDV | End Diastolic Volume measured in parasternal long-axis view |
| LVEF | (LVEDV − LVESV)/LVEDV * 100% |

Results

The baseline echocardiographic characteristics at time of initial injection (Day 30 post-MI) for all enrolled animals in this report (n=9) as reported by the echocardiography core laboratory, are provided in Table 5 below.

TABLE 5

Baseline characteristics

| Parameter | Baseline Value Group 1 | Baseline Value Group 2 | Baseline Value Group 3 |
|---|---|---|---|
| LVESV | 78 ± 18 ml | 67 ± 2 ml | 86 ± 31 ml |
| LVEDV | 132 ± 30 ml | 114 ± 11 ml | 130 ± 36 ml |
| LVEF | 41 ± 1% | 41 ± 5% | 34 ± 10% |

Table 5 shows the LVESV, LVEF and LVEDV at 0 and 30 days post-initial injection. Control PBS animals demonstrated an increase in LVESV and LVEDV and no improvement in LVEF consistent with this heart failure model. The treatment groups did not reduce cardiac volumes or increase LVEF compared to control. Similar results were obtained at 60 days post-initial injection.

Comparative Example 2

A strategy to augment stem cell homing to the periinfarct region by catheter-based transendocardial delivery of SDF-1 in a porcine model of myocardial infarction was investigated to determine if it would improve left ventricular perfusion and function. The catheter-based approach has been used successfully for cell transplantation and delivery of angiogenic growth factors in humans.

Female German landrace pigs (30 kg) were used. After an overnight fast, animals were anesthetized and intubated.

A 7 French sheath was placed in the femoral artery with the animal in a supine position. An over-the-wire balloon was advanced to the distal LAD. The balloon was inflated with 2 atm and agarose beads were injected slowly over 1 min via the balloon catheter into the distal LAD. After 1 minute the balloon was deflated and the occlusion of the distal LAD was documented by angiography. After induction of myocardial infarction animals were monitored for 3-4 h until rhythm and blood pressure was stable. The arterial sheath was removed, carprofen (4 mg/kg) was administered intramuscularly and the animals were weaned from the respirator. Two weeks after myocardial infarction animals were anesthetized. Electromechanical mapping of the left ventricle was performed via an 8F femoral sheath with the animal in the supine position. After a complete map of the left ventricle had been obtained, human SDF-1 (Peprotec, Rocky-Hill, N.J.) was delivered by 18 injections (5 µg in 100 µml saline) into the infarct and periinfarct region via an injection catheter. 5 µg per injection was used to adjust for the reported efficiency of the catheter injection. Injections were performed slowly over 20 s and only when the catheter's tip was perpendicular) to the left ventricular wall, when loop stability was <2 mm and when needle protrusion into the myocardium provoked ectopic ventricular extra beats. Control animals underwent an identical procedure with sham injections. Echocardiography excluded postinterventional pericardial effusion.

Twenty (20) animals completed the study protocol: 8 control animals and 12 SDF-1 treated animals. For myocardial perfusion imaging only 6 control animals could be evaluated due to technical problems. Infarct location was anteroseptal in all animals.

Infarct size in percent of the left ventricle as determined by tetrazolium staining was 8.9±2.6% in the control group and 8.9±1.2% in the SDF-1 group. Left ventricular muscle volume was similar in both groups (83±14 ml versus 95±10 ml, p=ns). Immunofluorescence staining revealed significantly more vWF-positive vessels in the peri-infarct area in SDF-1 treated animals than in control animals (349±17/mm$^2$ vs. 276±21/mm$^2$, p<0.05). A profound loss of collagen in the periinfarct area was observed in SDF-1 treated animals as compared to control animals (32±5% vs. 61±6%, p<0.005). The number of inflammatory cells (neutrophils and macrophages) within the periinfarct area was similar in both groups (332±51/mm$^2$ vs. 303±55/mm$^2$, p=ns). Global myocardial perfusion did not change from baseline to follow-up SPECT and there was no difference between groups. Final infarct size was similar in both groups and compared well to the results of tetrazolium staining Segmental analysis of myocardial perfusion revealed decreased tracer uptake in apical and anteroseptal segments with significant differences between myocardial segments. However, tracer uptake at baseline and follow-up were nearly identical in control and SDF-1 treated animals. There were no differences in end diastolic and end systolic volumes between groups. However, stroke volume increased in control animals and decreased slightly in SDF-1 treated animals. The difference between both groups was significant.

Similarly, ejection fraction increased in control animals and decreased in SDF-1 treated animals. The difference between groups showed a strong trend (p=0.05). Local shortening, another parameter of ventricular mechanical function, did not change in control animals. However, local shortening decreased significantly in SDF-1 treated animals, resulting in a significant difference between groups. There were no significant differences in unipolar voltage within and between groups. Significant correlations between baseline ejection fraction and stroke volume and baseline local shortening (EF and LS: r=0.71, SV and LS: r=0.59) were noted. Similar results were obtained for follow-up values (EF and LS: r=0.49, SV and LS: r=0.46). The change in local shortening correlated significantly with the change in ejection fraction (r=0.52) and stroke volume (r=0.46). There was neither a correlation between local shortening and enddiastolic volume (baseline r=−0.03, follow-up r=0.12) nor between ejection fraction and enddiastolic volume (baseline r=−0.04, follow-up r=0.05). Segmental analysis of EEM data showed decreased unipolar voltage and local shortening in the anteroseptal segments with significant differences between myocardial segments at baseline. The distribution of unipolar voltage values in myocardial segments was similar in both groups at baseline and at follow-up. Segmental local shortening did not change in the control group. However, it decreased in the SDF-1 group, mainly due to a decrease in the lateral and posterior segment of the left ventricle. There was a significant interaction between assignment to SDF-1 and follow-up vs. baseline.

The study described above demonstrated that a single application of SDF-1 protein was insufficient to produce functional cardiac benefit.

From the above description of the application, those skilled in the art will perceive improvements, changes and modifications. Such improvements, changes and modifications within the skill of the art are intended to be covered by the appended claims. All patents, patent applications and publications cited herein are incorporated by reference in their entirety.

What is claimed:

1. A stromal cell-derived factor 1 (SDF-1) plasmid having the polynucleotide sequence of the plasmid deposited with the American Type Culture Collection as accession number PTA-13320.

2. A preparation comprising an SDF-1 plasmid according to claim 1 and a pharmaceutically acceptable carrier.

3. The preparation according to claim 2, wherein said preparation is injectable.

4. The injectable preparation according to claim 3, wherein said pharmaceutically acceptable carrier is 5% dextrose.

5. The injectable preparation according to claim 3, comprising from about 0.33 mg/ml to about 5 mg/ml of said SDF-1 plasmid.

6. The injectable preparation according to claim 5, comprising about 2 mg/ml of said SDF-1 plasmid.

\* \* \* \* \*